US009611487B2

(12) United States Patent
Blake et al.

(10) Patent No.: US 9,611,487 B2
(45) Date of Patent: Apr. 4, 2017

(54) CELL-FREE SYSTEM FOR CONVERTING METHANE INTO FUEL AND CHEMICAL COMPOUNDS

(71) Applicant: GreenLight Biosciences, Inc., Medford, MA (US)

(72) Inventors: William Jeremy Blake, Winchester, MA (US); James R. Swartz, Menlo Park, CA (US)

(73) Assignee: GreenLight Biosciences, Inc., Medford, MA (US)

( * ) Notice: Subject to any disclaimer, the term of this patent is extended or adjusted under 35 U.S.C. 154(b) by 123 days.

(21) Appl. No.: 14/137,524

(22) Filed: Dec. 20, 2013

(65) Prior Publication Data

US 2014/0193869 A1    Jul. 10, 2014

Related U.S. Application Data

(60) Provisional application No. 61/740,972, filed on Dec. 21, 2012.

(51) Int. Cl.
| | | |
|---|---|---|
| C12P 7/16 | (2006.01) | |
| C12P 7/40 | (2006.01) | |
| C12P 7/64 | (2006.01) | |

(52) U.S. Cl.
CPC ........ *C12P 7/16* (2013.01); *C12P 7/40* (2013.01); *C12P 7/649* (2013.01); *Y02E 50/10* (2013.01); *Y02E 50/13* (2013.01)

(58) Field of Classification Search
None
See application file for complete search history.

(56) References Cited

U.S. PATENT DOCUMENTS

| | | |
|---|---|---|
| 3,223,592 A | 12/1965 | Sakaguchi et al. |
| 4,248,966 A | 2/1981 | Demain et al. |
| 4,266,034 A * | 5/1981 | Patel .................... C07D 301/02 435/190 |
| 4,946,783 A | 8/1990 | Beckwith et al. |
| 5,001,055 A | 3/1991 | Imahori et al. |
| 5,593,856 A | 1/1997 | Choi et al. |
| 5,665,566 A | 9/1997 | LaVallie |
| 6,159,693 A | 12/2000 | Shultz et al. |
| 6,168,931 B1 | 1/2001 | Swartz et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,994,986 B2 | 2/2006 | Swartz et al. |
| 7,041,479 B2 | 5/2006 | Swartz et al. |
| 7,312,049 B2 | 12/2007 | Calhoun et al. |
| 7,351,563 B2 | 4/2008 | Swartz et al. |
| 8,859,247 B2 | 10/2014 | Koltermann et al. |
| 8,916,358 B2 | 12/2014 | Swartz |
| 8,956,833 B2 | 2/2015 | Swartz |
| 9,469,861 B2 | 10/2016 | Blake et al. |
| 2002/0058303 A1 | 5/2002 | Swartz et al. |
| 2002/0160459 A1 | 10/2002 | Berry et al. |
| 2003/0040086 A1 | 2/2003 | Dodge et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2009/0053779 A1 | 2/2009 | Lee et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0325245 A1 | 12/2009 | Soucaille et al. |
| 2010/0120105 A1 | 5/2010 | Anthony et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |

(Continued)

FOREIGN PATENT DOCUMENTS

| | | |
|---|---|---|
| CN | 1329506 C | 8/2007 |
| EP | 1 433 856 A1 | 6/2004 |

(Continued)

OTHER PUBLICATIONS

International Search Report and Written Opinion for PCT/US2012/054195, mailed Apr. 12, 2013.
International Search Report and Written Opinion for PCT/US2011/035639, mailed Nov. 18, 2011.
International Preliminary Report on Patentability for PCT/US2011/035639, mailed Nov. 22, 2012.
International Search Report and Written Opinion for PCT/US2011/049997, mailed Dec. 13, 2011.
International Preliminary Report on Patentability for PCT/US2011/049997, mailed Mar. 14, 2013.
Extended European Search Report for Ep 09836804.6, mailed Jun. 4, 2012.

(Continued)

*Primary Examiner* — Robert Yamasaki
(74) *Attorney, Agent, or Firm* — Wolf, Greenfield & Sacks, P.C.

(57) ABSTRACT

The present disclosure relates, in some aspects, to cell-free methods and systems for large-scale conversion of methane to isobutanol, comprising combining, in a bioreactor at elevated pressure, methane, oxygen, and cell lysates containing methane monooxygenase, methanol dehydrogenase, and enzymes that catalyze the conversion of formaldehyde to isobutanol, to form a cell-free reaction mixture, and incubating under suitable conditions the cell-free reaction to convert methane to isobutanol.

29 Claims, 7 Drawing Sheets

(56) References Cited

U.S. PATENT DOCUMENTS

| | | |
|---|---|---|
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2015/0037868 A1 | 2/2015 | Blake et al. |
| 2015/0064751 A1 | 3/2015 | Swartz |
| 2015/0191753 A1 | 7/2015 | Swartz |
| 2016/0115558 A1 | 4/2016 | Swartz |

FOREIGN PATENT DOCUMENTS

| | | |
|---|---|---|
| EP | 2 204 453 A1 | 7/2010 |
| GB | 2 018 822 A | 10/1979 |
| JP | S61-260895 A | 11/1986 |
| JP | S63-7788 A | 1/1988 |
| JP | H01-228473 A | 9/1989 |
| JP | H07-298893 A | 11/1995 |
| JP | H08-502176 A | 3/1996 |
| JP | H08-196284 A | 8/1996 |
| JP | 2002-535008 A | 10/2002 |
| JP | 2007-534338 A | 11/2007 |
| JP | 2009-531050 A | 9/2009 |
| WO | WO 00/39288 A1 | 7/2000 |
| WO | WO 00/44923 A1 | 8/2000 |
| WO | WO 00/55353 A1 | 9/2000 |
| WO | WO 03/038117 A2 | 5/2003 |
| WO | WO 2005/030949 | 4/2005 |
| WO | WO 2005/098048 A1 | 10/2005 |
| WO | WO 2006/001382 | 1/2006 |
| WO | WO 2006/090385 | 8/2006 |
| WO | WO 2007/053655 A2 | 5/2007 |
| WO | WO 2007/110619 A1 | 10/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2010/074760 A1 | 7/2010 |
| WO | WO 2010/077806 A1 | 7/2010 |
| WO | WO 2011/140516 A2 | 11/2011 |
| WO | WO 2012/030980 A1 | 3/2012 |
| WO | WO 2012/135902 | 10/2012 |
| WO | WO 2014/197655 | 12/2014 |

OTHER PUBLICATIONS

International Search Report and Written Opinion for PCT/US2009/067841, mailed Mar. 22, 2010.
International Preliminary Report on Patentability for PCT/US2009/067841, mailed Jun. 30, 2011.
International Search Report and Written Opinion for PCT/US2009/006704, mailed Mar. 3, 2010.
International Preliminary Report on Patentabilityfor PCT/US2009/006704, mailed Jul. 7, 2011.
Alber et al., Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.

Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Calhoun et al., An economical method for cell-free protein synthesis using glucose and nucleoside monophosphates. Biotechnol Prog. Jul.-Aug. 2005;21(4):1146-53.
Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 2007;375(2):3-17.
Calhoun et al., Total amino acid stabilization during cell-free protein synthesis reactions. J Biotechnol. May 17, 2006;123(2):193-203. Epub Jan. 26, 2006.
Daniell et al., Transformation of the cyanobacterium Anacystis nidulans 6301 with the *Escherichia coli* plasmid pBR322. Proc Natl Acad Sci U S A. Apr. 1986;83(8):2546-50.
De Mey et al., Construction and model-based analysis of a promoter library for *E. coli:* an indispensable tool for metabolic engineering. BMC Biotechnol. Jun. 18, 2007;7:34.
De Vries et al., Cloning, expression, and sequence analysis of the Bacillus methanolicus C1 methanol dehydrogenase gene. J Bacteriol. Aug. 1992;174(16):5346-53.
Fischer et al., Metabolic flux profiling of *Escherichia coli* mutants in central carbon metabolism using GC-MS. Eur J Biochem. Mar. 2003;270(5):880-91.
Flores et al., Pathway engineering for the production of aromatic compounds in *Escherichia coli*. Nat Biotechnol. May 1996;14(5):620-3.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fox et al., Methane monooxygenase from Methylosinus trichosporium OB3b. Purification and properties of a three-component system with high specific activity from a type II methanotroph. J Biol Chem. Jun. 15, 1989;264(17):10023-33.
Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.
Gosset et al., A direct comparison of approaches for increasing carbon flow to aromatic biosynthesis in *Escherichia coli*. J Ind Microbiol. Jul. 1996;17(1):47-52.
Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s00253-009-1866-2. Epub Feb. 12, 2009.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1):19-26.
Kern et al., Engineering primary metabolic pathways of industrial micro-organisms. J Biotechnol. Mar. 30, 2007;129(1):6-29. Epub Dec. 2, 2006.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Lee et al., Fermentative production of thymidine by a metabolically engineered *Escherichia coli* strain. Appl Environ Microbiol. Apr. 2009;75(8):2423-32. Epub Feb. 27, 2009.
Lee et al., Systems metabolic engineering of *Escherichia coli* for L-threonine production. Mol Syst Biol. 2007;3:149. Epub Dec. 4, 2007.
Mackle et al., Role of signal peptides in targeting of proteins in cyanobacteria. J Bacteriol. Apr. 1994;176(7): 1857-64.

(56) References Cited

OTHER PUBLICATIONS

Meyerhof, New investigations in the kinetics of cell free alcoholic fermentation. Antonie Van Leeuwenhoek. Jan.-Apr. 1947;12(1-4):140-4.

Meynial-Salles et al., New tool for metabolic pathway engineering in *Escherichia coli:* one-step method to modulate expression of chromosomal genes. Appl Environ Microbiol. Apr. 2005;71(4):2140-4.

Michel-Reydellet et al., Amino acid stabilization for cell-free protein synthesis by modification of the *Escherichia coli* genome. Metab Eng. Jul. 2004;6(3):197-203.

Patnaik et al., Engineering of *Escherichia coli* central metabolism for aromatic metabolite production with near theoretical yield. Appl Environ Microbiol. Nov. 1994;60(11):3903-8.

Pitera et al., Balancing a heterologous mevalonate pathway for improved isoprenoid production in *Escherichia coli*. Metab Eng. Mar. 2007;9(2):193-207. Epub Nov. 23, 2006.

Reyes et al., Genomic library screens for genes involved in n-butanol tolerance in *Escherichia coli*. PloS One. Mar. 8, 2011;6(3):e17678.

Scopes, Glycolysis in cell-free systems. New beer in an old bottle: Eduard Buchner and the growth of biochemical knowledge. Ed A. Cornish-Bowden. 1997;151-8.

Stephanopoulos et al., Exploiting biological complexity for strain improvement through systems biology. Nat Biotechnol. Oct. 2004;22(10):1261-7.

Swartz, Developing cell-free biology for industrial applications. J Ind Microbiol Biotechnol. Jul. 2006;33(7):476-85. Epub May 9, 2006. Review.

Swartz, Transforming biochemical engineering with cell-free biology. AIChE J. 2012;58(1):5-13.

Sybesma et al., Increased production of folate by metabolic engineering of Lactococcus lactis. Appl Environ Microbiol. Jun. 2003;69(6):3069-76.

Tracewell et al., Directed enzyme evolution: climbing fitness peaks one amino acid at a time. Curr Opin Chem Biol. Feb. 2009;13(1):3-9. Epub Feb. 25, 2009.

Tyo et al., Analysis of polyhydroxybutyrate flux limitations by systematic genetic and metabolic perturbations. Metab Eng. May 2010;12(3):187-95. Epub Oct. 30, 2009.

Wang et al., Programming cells by multiplex genome engineering and accelerated evolution. Nature. Aug. 13, 2009;460(7257):894-8. Epub Jul. 26, 2009.

Ward et al., Genomic insights into methanotrophy: the complete genome sequence of Methylococcus capsulatus (Bath). PLOS Biology. 2004;2(10):1616-28.

Welch et al., Studies on cell-free metabolism: Ethanol production by a yeast glycolytic system reconstituted from purified enzymes. J Biotechnol. 1985;2:257-73.

Wiechert et al., A universal framework for 13C metabolic flux analysis. Metab Eng. Jul. 2001;3(3):265-83.

Wiechert, $^{13}$C metabolic flux analysis. Metab Eng. Jul. 2001;3(3):195-206.

Yu et al., Production of high-quality particulate methane monooxygenase in high yields from Methylococcus capsulatus (bath) with a hollow-fiber membrane bioreactor. J Bacteriol. Oct. 2003;185(20):5915-24.

Zamboni et al., $^{13}$C-based metabolic flux analysis. Nat Protoc. 2009;4(6):878-92. Epub May 21, 2009.

International Preliminary Report on Patentability for PCT/US2014/049805, mailed Feb. 18, 2016.

International Preliminary Report on Patentability for PCT/US2012/054195, mailed Mar. 20, 2014.

Invitation to Pay Additional Fees for PCT/US2013/077238, mailed Mar. 18, 2014.

International Search Report and Written Opinion for PCT/US2013/077238, mailed May 19, 2014.

Invitation to Pay Additional Fees for PCT/US2014/049805, mailed Nov. 14, 2014.

International Search Report for PCT/US2014/049805, mailed Feb. 16, 2015.

International Preliminary Report on Patentability for PCT/US2013/077238, mailed Jul. 2, 2015.

International Search Report and Written Opinion for PCT/US2014/041009, mailed Sep. 10, 2014.

International Preliminary Report on Patentability for PCT/US2014/041009, mailed Dec. 17, 2015.

[No Author Listed] Crude Lysate. Wikipedia entry for Crude Lysate, http://en.wikipedia.org/wiki/Crude_lysate downloaded on Mar. 3, 2015. Page Last Modified on Nov. 3, 2013. 1 page.

Bujara et al., Exploiting cell-free systems: Implementation and debugging of a system of biotransformations. Biotechnol Bioeng. Jun. 15, 2010;106(3):376-89. doi: 10.1002/bit.22666.

Danese et al., Targeting and assembly of periplasmic and outer-membrane proteins in *Escherichia coli*. Annu Rev Genet. 1998;32:59-94.

Daube et al., Cell-free co-synthesis of protein nanoassemblies: tubes, rings, and doughnuts. Nano Lett. Mar. 2007;7(3):638-41. Epub Feb. 2, 2007.

Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.

Egan et al., Transketolase kinetics. The slow reconstitution of the holoenzyme is due to rate-limiting dimerization of the subunits. J Biol Chem. May 25, 1981;256(10):4877-83.

Eser et al.,Target-directed proteolysis in vivo. Methods Enzymol. 2007;421:68-83.

Fujio et al., Production of ATP from Adenine by Brevibacterium ammoniagenes, J Ferment Technol. 1983;61(3):261-267.

Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04.001. Epub May 2, 2008.

Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s0025 3-009-1866-2. Epub Feb. 12, 2009.

Hryniewicz et al., Sulfate and thiosulfate transport in *Escherichia coli* K-12: identification of a gene encoding a novel protein involved in thiosulfate binding. J Bacteriol. Jun. 1990;172(6):3358-66.

Jenny et al., A critical review of the methods for cleavage of fusion proteins with thrombin and factor Xa. Protein Expr Purif. Sep. 2003;31(1):1-11.

Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.

Kim et al., Metabolic flux analysis for calcium dependent antibiotic (CDA) production in Streptomyces coelicolor. Metab Eng. Oct. 2004;6(4):313-25.

Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.

Krutsakorn et al., In vitro production of n-butanol from glucose. Metab Eng. Nov. 2013;20:84-91. doi: 10.1016/j.ymben.2013.09.006. Epub Sep. 19, 2013.

Mayes, Metabolism of Glycogen. In: Harper's Biochemistry—a LANGE medical book. 1990. Twenty-second edition. Murray et al., Eds. Chapter 20: 171-178.

Ninh et al., Assembly and multiple gene expression of thermophilic enzymes in *Escherichia coli* for in vitro metabolic engineering. Biotechnol Bioeng. Jul. 26, 2014. doi: 10.1002/bit.25338.

Noireaux et al., Principles of cell-free genetic circuit assembly. Proc Natl Acad Sci U S A. Oct. 28, 2003;100(22):12672-7. Epub Oct. 14, 2003.

Pace et al., Photosynthetic regeneration of ATP using bacterial chromatophores. Biotechnol Bioeng. Oct. 1976;18(10):1413-23.

Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.

(56) References Cited

OTHER PUBLICATIONS

Peralta-Yahya et al., Microbial engineering for the production of advanced biofuels. Nature. Aug. 16, 2012;488(7411):320-8. doi: 10.1038/nature11478.
Romanowski et al., Crystal structure of the *Escherichia coli* shikimate kinase I (AroK) that confers sensitivity to mecillinam. Proteins. Jun. 1, 2002;47(4):558-62.
Schierle et al., The DsbA signal sequence directs efficient, cotranslational export of passenger proteins to the *Escherichia coli* periplasm via the signal recognition particle pathway. J Bacteriol. Oct. 2003;185(19):5706-13.
Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.
Sroga et al., Periplasmic expression as a basis for whole cell kinetic screening of unnatural enzyme reactivities. Methods Enzymol. 2004;388:145-56.
Stapon et al., Carbapenem biosynthesis: confirmation of stereochemical assignments and the role of CarC in the ring stereoinversion process from L-proline. J Am Chem Soc. Jul. 16, 2003;125(28):8486-93.
Thony-Meyer et al., Translocation to the periplasm and signal sequence cleavage of preapocytochrome c depend on sec and lep, but not on the ccm gene products. Eur J Biochem. Jun. 15, 1997;246(3):794-9.
Ye et al., Synthetic metabolic engineering—a novel, simple technology for designing a chimeric metabolic pathway. Microb Cell Fact. Sep. 6, 2012;11:120. doi: 10.1186/1475-2859-11-120.
Extended European Search Report for EP09835395.6 mailed Mar. 16, 2016.
Invitation to Pay Additional Fees for PCT/US2016/023173, mailed Jul. 8, 2016.
International Search Report and Written Opinion for PCT/US2016/023173, mailed Sep. 16, 2016.
International Search Report and Written Opinion for PCT/US2016/024937, mailed Sep. 9, 2016.
GenBank Accession No. AAC43119. Sep. 3, 1993. 4 pages. Last accessed Jul. 26, 2016.
Blattner et al., Analysis of the *Escherichia coli* genome. IV. DNA sequence of the region from 89.2 to 92.8 minutes. Nucleic Acids Res. Nov. 25, 1993;21(23):5408-17.
Brady et al.,Transfer of Pantoea citrea, Pantoea punctata and Pantoea terrea to the genus *Tatumella emend.* as *Tatumella citrea* comb. nov., *Tatumella punctata* comb. nov. and *Tatumella terrea* comb. nov. and description of *Tatumella morbirosei* sp. nov. Int J Syst Evol Microbiol. Mar. 2010;60(Pt 3):484-94. doi: 10.1099/ijs.0.012070-0. Epub Aug. 4, 2009.
Chisti et al., Disruption of microbial cells for intracellular products. Enzyme Micro Technol 1986;8(4):194-204. doi 10.1016/0141-0229(86)90087-6.
Ehrmann et al., TnTIN and TnTAP: mini-transposons for site-specific proteolysis in vivo. Proc Natl Acad Sci U S A. Nov. 25, 1997;94(24):13111-5.
Goody, A simple and rapid method for the synthesis of nucleoside 5'-monophosphates enriched with 170 or 180 on the phosphate group. Anal Biochem. Jan. 15, 1982;119(2):322-4.
Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.
Kawarasaki et al., Prolonged cell-free protein synthesis in a batch system using wheat germ extract.Biosci Biotechnol Biochem. Oct. 1994;58(10):1911-3.
Kim et al., Regeneration of adenosine triphosphate from glycolytic intermediates for cell-free protein synthesis.Biotechnol Bioeng. Aug. 20, 2001;74(4):309-16.
Klemme, Photoproduction of hydrogen by purple bacteria:A critical evaluation of the rate limiting enzymatic steps. J Bioscience 1993;48 482-87.
Li et al., Rational strain improvement for enhanced clavulanic acid production by genetic engineering of the glycolytic pathway in Streptomyces clavuligerus. Metab Eng. May 2006;8(3):240-52. Epub Mar. 10, 2006.
Liu et al., Combined biosynthetic pathway for de novo production of UDP-galactose: catalysis with multiple enzymes immobilized on agarose beads. Chembiochem. Apr. 2, 2002;3(4):348-55.
Pines et al., Expression and secretion of proteins in *E. coli*. Mol Biotechnol. Aug. 1999;12(1):25-34.
Schultheisz et al., Pathway engineered enzymatic de novo purine nucleotide synthesis. ACS Chem Biol. Aug. 15, 2008;3(8):499-511. doi: 10.1021/cb800066p.
Scopes, Studies with a reconstituted muscle glycolytic system. The anaerobic glycolytic response to simulated tetanic contraction. Biochem J. Jan. 1974;138(1):119-23.
Spickler et al., Action of RNase II and polynucleotide phosphorylase against RNAs containing stem-loops of defined structure. J Bacteriol. May 2000;182(9):2422-7.
Spirin, High-throughput cell-free systems for synthesis of functionally active proteins.Trends Biotechnol. Oct. 2004;22(10):538-45. With Supplementary data.
Stazic et al., Antisense RNA protects mRNA from RNase E degradation by RNA-RNA duplex formation during phage infection. Nucleic Acids Res. Jun. 2011;39(11):4890-9. doi: 10.1093/nar/gkr037. Epub Feb. 15, 2011.
Swartz, Universal cell-free protein synthesis. Nat Biotechnol. Aug. 2009;27(8):731-2. doi: 10.1038/nbt0809-731.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Zago et al., Cloning and characterization of polyphosphate kinase and exopolyphosphatase genes from Pseudomonas aeruginosa 8830. Appl Environ Microbiol. May 1999;65(5):2065-71.
Zhao et al., A novel high-throughput screening method for microbial transglutaminases with high specificity toward Gln141 of human growth hormone. J Biomol Screen. Feb. 2010;15(2):206-12. doi: 10.1177/1087057109356206. Epub Jan. 19, 2010.

* cited by examiner glucose + 3 ATP + 2 NAD(P)H → isoprene + 3 ADP + 2 NAD(P)⁺ + CO₂ + H₂O + 3 Pi ↳ Source of ATP and reducing equivalents required
 ➢ obtain from methane oxidation glucose + 1.75 CH₄ + 2.5 O₂ → isoprene + 2.75 CO₂ + 5.5 H₂O 7.75 methane + 8.5 O₂ → isoprene + 2.75 CO₂ + 11.5 H₂O

CELL-FREE SYSTEM FOR CONVERTING METHANE INTO FUEL AND CHEMICAL COMPOUNDS

RELATED APPLICATIONS

This application claims priority under 35 U.S.C. §119(e) to U.S. provisional application, U.S. Ser. No. 61/740,972, filed Dec. 21, 2012, which is incorporated by reference herein in its entirety.

BACKGROUND OF INVENTION

Isobutanol is produced naturally during the fermentation of carbohydrates and may also be a byproduct of the decay process of organic matter (Atsumi et al. 2008 *Nature* 451: 86-89). The biosynthetic pathway used to produce isobutanol was first discovered in species of bacteria from the genus *Clostridium*. This pathway has been genetically engineered into several species of microorganisms which are more easily manipulated by current scientific methods than microorganisms of the genus *Clostridium* (Peralta-Yahya et al. 2012 *Nature* 488: 320-328).

SUMMARY OF INVENTION

The present invention provides a cell-free system for the conversion of natural gas, in particular, methane, to target biofuels (e.g., isobutanol) and other chemical compounds. Natural gas is a hydrocarbon gas mixture of primarily methane, but also includes varying amounts of other higher alkanes and a lesser percentage of carbon dioxide, nitrogen, and hydrogen sulfide. Aspects of the invention uniquely combine biosynthetic and chemical engineering processes to provide a cell-free biosynthetic system capable of producing from natural gas greater than, for example, 10 g to 25 g biofuel per liter-hr. For example, an industrial or commercial plant sized to use a 155 m$^3$ reactor can produce greater than 30,000 metric tons of biofuel (e.g., isobutanol) per year (e.g., >500 BPD scale), in some instances with raw material costs of less than 20% of the product's value.

The cell-free process provided herein, in some embodiments, combines (i) a cell-free lysate from methane-metabolizing methanotrophs (e.g., *Methylococcus capsulatus* Bath) that express enzymes (e.g., methane monooxygenase, MMO) for the conversion of methane to methanol or formaldehyde with (ii) a cell-free lysate(s) from recombinant bacterial cells (e.g., *Escherichia coli*) that express enzymes for the conversion of methanol or formaldehyde to biofuel or other chemical compound. The cell lysates are combined with methane and oxygen, both required for MMO activation, in a pressurized bioreactor (e.g., at least 1 bar) to drive the transformation of methane to biofuel or other chemical compound. The cell-free process of the present disclosure typically uses a multiphase reaction system that is particularly useful for delivering methane and oxygen to exposed lipid bilayer membranes (e.g., of intracellular membrane vesicles of the cell lysate(s)) by first diffusing the gases into an aqueous phase. In some embodiments, enzymes for the conversion of methane to formaldehyde and/or for the conversion of formaldehyde to biofuel or other chemical compound are added exogenously to the cell-free system. Such exogenously added enzymes may be purified or partially purified.

It should be understood that while the present disclosure describes the use of methanotrophs for the expression/production of enzymes for the conversion of methane to formaldehyde, other organisms for use in producing enzymes for the conversion of methane to formaldehyde are contemplated herein.

In some aspects, provided herein are cell-free methods for large-scale conversion of methane to a biofuel or other chemical compound comprising: combining, in a bioreactor at elevated pressure, one or more cell lysates containing enzyme(s) that catalyze the conversion of methane to formaldehyde, and enzymes that catalyze the conversion of formaldehyde to a biofuel or another chemical compound, methane, and oxygen to form a cell-free reaction mixture; and incubating under suitable conditions (e.g., high pressure, 37° C.) the cell-free reaction to convert methane to a biofuel or other chemical compound. In some embodiments, the bioreactor may further comprise an organic solvent (e.g., decane). In some embodiments, the organic phase is saturated or supersaturated with methane. "Suitable conditions" include, without limitation, a pressure of at least 1 bar (e.g., 1 bar to 10 bar, or 5 bar to 10 bar) and/or a temperature of 35° C. to 40° C. (e.g., 37° C.).

In some embodiments, provided herein are cell-free methods for large-scale conversion of methane to isobutanol comprising: combining, in a bioreactor at elevated pressure, one or more cell lysates containing methane monooxygenase and methanol dehydrogenase (e.g., a recombinant NAD-linked methanol dehydrogenase), which catalyze the conversion of methane to formaldehyde, and one or more of hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, pyruvate kinase, acetolactate synthase, acetohydroxy acid isomeroreductase, dihydroxy acid dehydratase, alpha-ketoisovalerate decarboxylase, and isobutanol dehydrogenase, which catalyze the conversion of formaldehyde to isobutanol, methane, and oxygen to form a cell-free reaction mixture; and incubating under suitable conditions the cell-free reaction to convert methane to isobutanol. In some embodiments, the bioreactor may further comprise an organic solvent (e.g., decane).

One of the intermediate products of the conversion formaldehyde to biofuel or other chemical compound is pyruvate. Thus, in some aspects, provided herein are cell-free methods for large-scale conversion of methane to pyruvate comprising: combining, in a bioreactor at elevated pressure, one or more cell lysates containing enzyme(s) that catalyze the conversion of methane to formaldehyde, and enzymes that catalyze the conversion of formaldehyde to pyruvate, methane, and oxygen to form a cell-free reaction mixture; and incubating under suitable conditions the cell-free reaction to convert methane to pyruvate. In some embodiments, the bioreactor may further comprise an organic solvent (e.g., decane).

In some embodiments, provided herein are cell-free methods for large-scale conversion of methane to pyruvate comprising: combining, in a bioreactor at elevated pressure, one or more cell lysates containing methane monooxygenase and methanol dehydrogenase (e.g., a recombinant NAD-linked methanol dehydrogenase), which catalyze the conversion of methane to formaldehyde, and one or more of hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, and pyruvate kinase, which catalyze the conversion of formaldehyde to pyruvate, methane, and oxygen to form a cell-free reaction mixture; and incubating under suitable conditions the cell-free reaction to convert methane to pyruvate. In some embodiments, the bioreactor may further comprise an organic solvent (e.g., decane).

In other aspects, provided herein are cell-free systems and compositions for large-scale conversion of methane to a biofuel or other chemical compound comprising a bioreactor that comprises: a gas phase comprising methane and oxygen; and an aqueous phase comprising a cell lysate containing enzyme(s) that catalyze the conversion of methane to formaldehyde and enzymes that catalyze the conversion of formaldehyde to a biofuel or chemical compound. In some embodiments, the bioreactor further comprises an organic phase comprising an organic solvent (e.g., decane).

In some embodiments, provided herein are cell-free systems and compositions for large-scale conversion of methane to isobutanol comprising a bioreactor that comprises: a gas phase comprising methane and oxygen; and an aqueous phase comprising one or more cell lysates containing methane monooxygenase, and methanol dehydrogenase (e.g., a recombinant NAD-linked methanol dehydrogenase), which catalyze the conversion of methane to formaldehyde and hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, pyruvate kinase, acetolactate synthase, acetohydroxy acid isomeroreductase, dihydroxy acid dehydratase, alpha-ketoisovalerate decarboxylase, and isobutanol dehydrogenase, which catalyze the conversion of formaldehyde to isobutanol. In some embodiments, the bioreactor further comprises an organic phase comprising an organic solvent (e.g., decane).

In some embodiments, provided herein are cell-free systems and compositions for large-scale conversion of methane to pyruvate comprising a bioreactor that comprises: a gas phase comprising methane and oxygen; and an aqueous phase comprising one or more cell lysates containing methane monooxygenase and methanol dehydrogenase (e.g., a recombinant NAD-linked methanol dehydrogenase), which catalyze the conversion of methane to formaldehyde, and hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, and pyruvate kinase, which catalyze the conversion of formaldehyde to pyruvate. In some embodiments, the bioreactor further comprises an organic phase comprising an organic solvent (e.g., decane).

In some aspects, provided herein are cell-free methods for large-scale conversion of methane to pyruvate, comprising: (a) expressing in methanotrophs one or more enzymes for the conversion of methane to formaldehyde, (b) expressing in recombinant bacteria one or more enzymes for the conversion of formaldehyde to pyruvate, (c) combining cell lysate from the methanotrophs and the recombinant bacteria with methane, an organic solvent (e.g., decane), and oxygen to form a cell-free reaction mixture, and (d) incubating under suitable conditions the cell-free reaction to convert methane to pyruvate. In some embodiments, the one or more enzymes for the conversion of methane to formaldehyde are selected from methane monooxygenase and methanol dehydrogenase. In some embodiments, the one or more enzymes for the conversion of formaldehyde to pyruvate are selected from hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, and pyruvate kinase.

In some embodiments, the method further comprises lysing the methanotroph and/or recombinant bacterial cells (e.g., prior to the combining step).

In some embodiments, the method further comprises expressing in the recombinant bacterial cells a protease that cleaves and inactivates an enzyme. For example, the protease may cleave and inactivate pyruvate dehydrogenase and/or formaldehyde dehydrogenase. Alternatively, the protease may be added exogenously.

Also provided herein are cell lysates that comprise one or more enzymes for the conversion of methane to formaldehyde, as well as cell lysates comprising one or more enzymes for the conversion of formaldehyde to a biofuel or other chemical compound. In some embodiments, the cell lysates comprise one or more enzymes for the conversion of formaldehyde to pyruvate, or one or more enzymes for the conversion of formaldehyde to isobutanol. Cell lysates may further comprise small molecules and cofactors (e.g., adenosine triphosphate, NAD(PH)), and salts, such as magnesium, for enzyme function.

Further provided herein are biofuels and other chemical compound or intermediate produced by any one or more of the cell-free processes described herein.

DETAILED DESCRIPTION OF THE INVENTION

Provided herein, in some embodiments, is a cell-free system for the conversion of natural gas, in particular methane, to a biofuel and other chemical compounds. The process combines cell-free lysates from methanotrophs with those from other recombinant bacteria in a reactor typically operated at high pressure (e.g., at least 1 bar, or at least 5 bar). The cell-free processes, systems, reactions mixtures, compositions, recombinant organisms, and nucleic acid constructs of the invention are considered parts of a platform technology enabling the efficient production of many different biofuels or other chemical compounds from methane or natural gas. The use of a cell-free biosynthetic system does not require the maintenance of cell viability, enables direct monitoring and adjustment of reaction parameters (e.g., substrate feed rates, temperature, pH, pressure, dissolved oxygen), provides a flexible reaction environment, and enables control of carbon and energy flux (see, e.g., International Publication Numbers WO 2010/077806 and WO 2012/030980, incorporated by reference herein). In some embodiments, the cell-free process of the invention addresses mass transfer challenges associated with methane and oxygen solubility by operating under high pressure, providing an organic phase in which methane has greater solubility, and increasing methane bubble and air bubble surface area by injecting gases at high pressure.

Generally, a cell-free process of the invention includes (i) use of methanotrophs to express enzymes (e.g., MMO) for the conversion of methane to formaldehyde, (ii) use of recombinant bacteria (e.g., $E. coli$) to express enzymes in biosynthetic pathways that produce biofuels and other chemical compounds and (iii) use of control systems and a reaction environment with flexibility that previously was only offered by chemical processes using inorganic catalysts.

Figure 1:
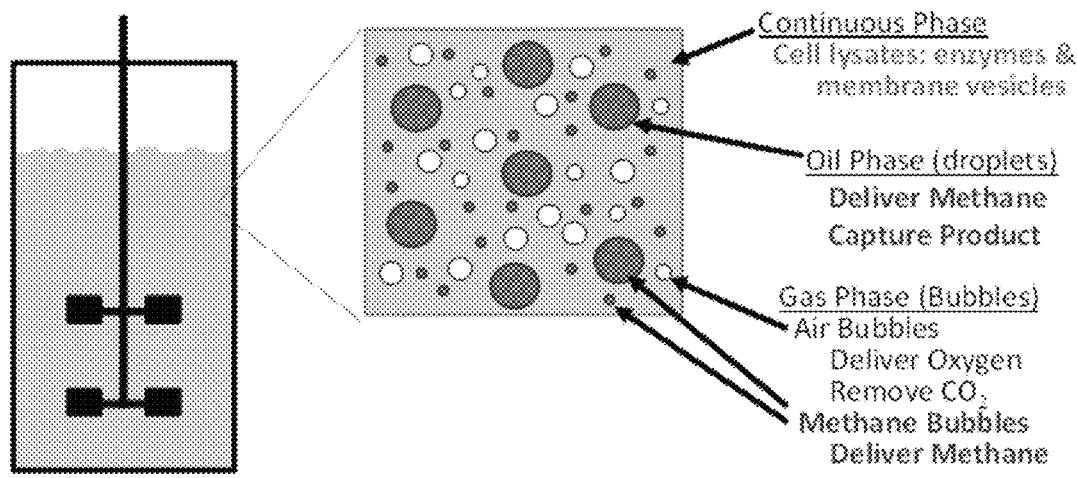
FIG. 1 shows a diagram of an exemplary cell-free multiphase reaction system of the invention designed to deliver methane and oxygen into the aqueous phase at a high rate.

Some aspects of the invention provide cell-free processes that use a multiphase reaction system, as shown in FIG. 1. The reaction mixture of the cell-free bioreactor includes, in some embodiments: (i) a gaseous phase to deliver methane and oxygen and to remove $CO_2$, and (ii) an aqueous, or continuous, phase that includes the enzymes and membrane vesicles. In some embodiments, the cell-free bioreactor also includes an organic (apolar) phase to deliver the natural gas (including methane) and to preferentially absorb the desired product (FIG. 1). In some embodiments, for example when an organic phase is included, the aqueous phase, includes an emulsion of the cell lysate (e.g., including enzymes and membrane vesicles of the cell contents), the gaseous phase (e.g., as air bubbles to deliver oxygen and remove $CO_2$ and as methane bubbles to deliver methane), and the organic phase (e.g., droplets of organic solvent to deliver methane and capture the product). In some embodiments, the emulsion is formed outside of the reactor. In other embodiments, the emulsion is formed via high pressure injection of an organic phase into the bioreactor. "High pressure," as used herein, refers to pressure that is at least 1 bar. For example, high pressure may refer to pressure that is at least 1 bar, at least 2 bar, at least 5 bar, or at least 10 bar. In some embodiments, high pressure may refer to a pressure that is 1 to 5 bar, 1 to 10 bar, or 5 to 10 bar.

The organic solvent of the organic phase may be an alkane. Examples of alkanes for use as provided herein include, without limitation, pentane, hexane, heptane, octane, nonane, and decane. Other organic solvents may be used. For example, organic solvents with the following properties are contemplated herein: (i) use of which results in less than 10% reduction in pyruvate production rate in cell-free reaction, and (ii) methane solubility greater than 25 mg/L to 30 mg/L (e.g., 23 mg/L) at atmospheric pressure.

Figure 2:
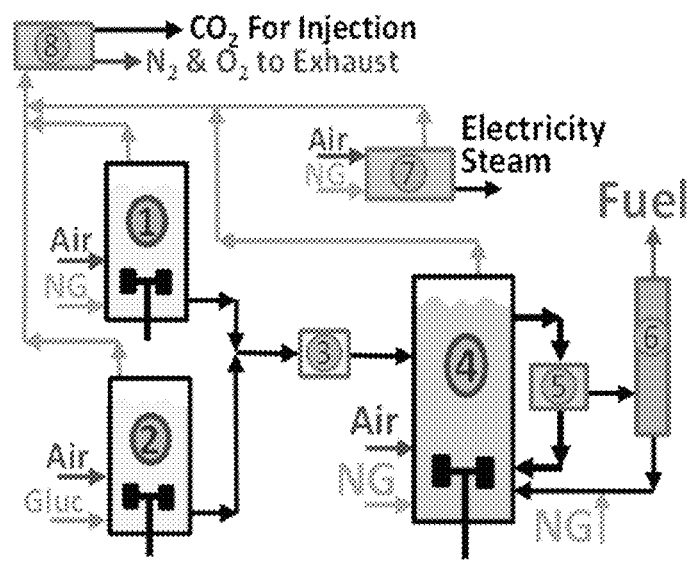
FIG. 2 shows a diagram of an exemplary cell-free transformation platform of the invention.

FIG. 2 shows a diagram of a non-limiting exemplary cell-free process of the present invention. Each step of the process is indicated numerically, 1-8. In step 1, recombinant methanotrophs express enzymes for the conversion of methane in natural gas to formaldehyde. In step 2, recombinant $Escherichia coli$ ($E. coli$) express enzymes for the conversion of formaldehyde to biofuel, in this case, isobutanol, and also provide a compartmentalized protease (see, e.g., International Publication Numbers WO 2010/077806 and WO 2012/030980, incorporated by reference herein). The protease, for example, cleaves a targeted formaldehyde dehydrogenase (expressed by the methanotroph) that has been engineered to contain a cognate protease recognition site. Formaldehyde dehydrogenase converts formaldehyde to formate, and therefore, it interferes with the conversion of formaldehyde to a biofuel or other chemical compound in a cell-free reaction system. Thus, when the organisms from step 1 and step 2 are lysed and combined in step 3, the protease is released from its cellular compartment (e.g., periplasm) and cleaves the formaldehyde dehydrogenase, thereby inactivating it. This inactivation of formaldehyde dehydrogenase increases the conversion yield of biofuel. The conversion of methane into the biofuel occurs in step 4, in an engineered and computer controlled bioreactor pressurized at, for example, 10 bar to drive mass transfer rates for a volumetric productivity of, for example, at least 1, at least 5, at least 10, at least 15, at least 20, or at least 25 g/liter-hr. The bioreactor of step 4 includes a multiphase fluid containing an aqueous phase to support the enzyme catalysts of the cell lysates and, optionally, an organic phase to help deliver the natural gas or methane and absorb the product biofuel. These phases, in some embodiments, are separated in step 5 to deliver the organic phase for fuel removal in step 6. In some embodiments, the organic phase is then recharged with natural gas (or methane) and injected back into the bioreactor at multiple points. Air and natural gas may be separately injected, in some embodiments. Further, in some instances, external heat exchangers as well as a cooling jacket remove process heat and control reactor temperature. To ensure safe operation, typically multiple temperature sensors throughout the reactor detect any "hot spots" possibly caused by spontaneous combustion. This triggers an immediate reduction in methane and/or air injection and a rebalancing of the distributed inlets.

It should be understood that some of the steps of the cell-free process may be carried out simultaneously or sequentially. For example, expression of enzymes for the conversion of methane to formaldehyde and expression of enzymes for the conversion of formaldehyde to biofuel may occur simultaneously (e.g., in separate compartments of a reactor) before cell lysis.

Figure 3:
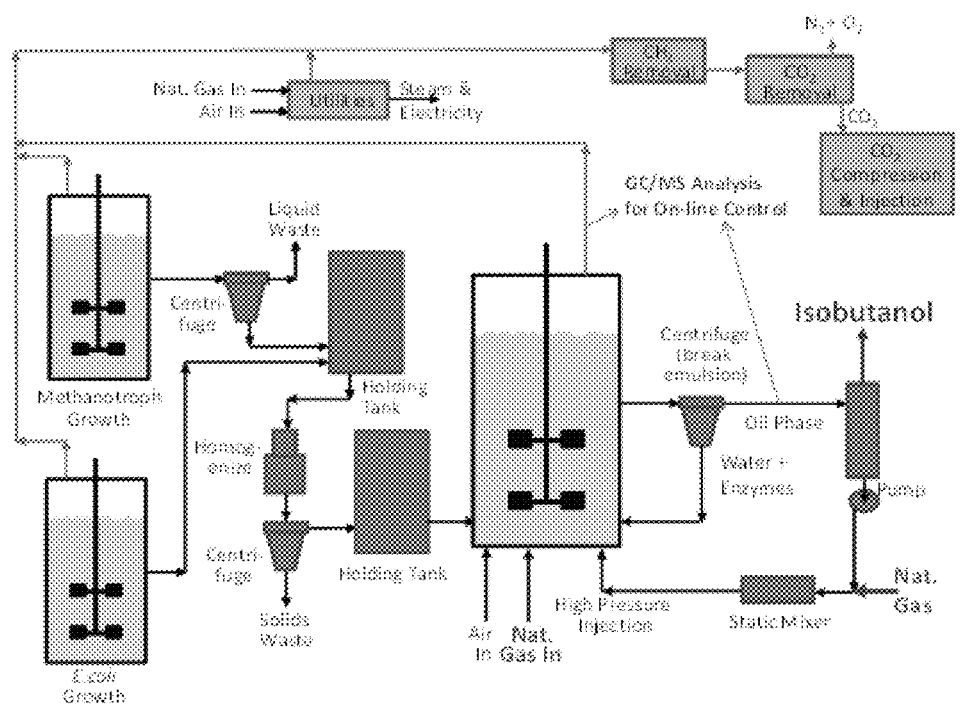
FIG. 3 shows a diagram of an exemplary cell-free transformation platform of the invention.
Figure 4:
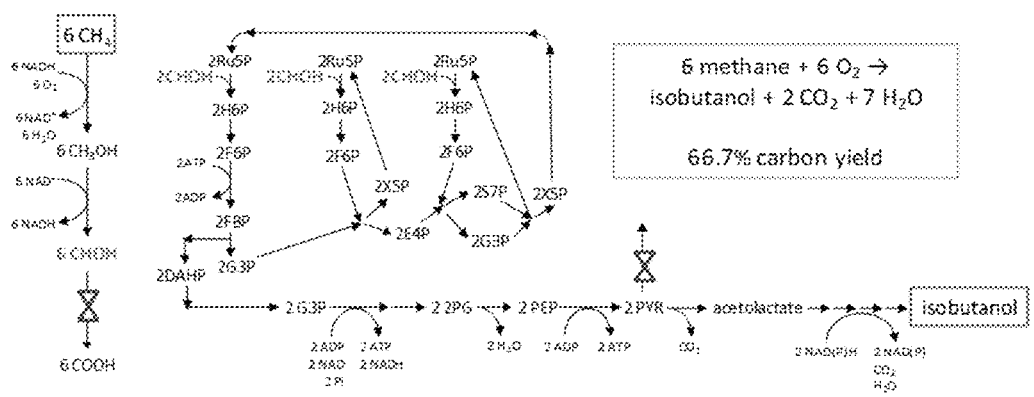
FIG. 4 shows a diagram of the isobutanol pathway.

FIG. 3 shows a diagram of another non-limiting example of a cell-free process of the present invention. For the sake of clarity, elements such as the inoculum preparation fermentors, compressors, coolers, heat exchangers, and pumps are not shown. In this example, the methanotrophs are concentrated by centrifugation before being combined with the uncentrifuged recombinant $E. coli$ culture. The combined cells are held in a chilled tank while waiting for lysis with a high pressure homogenizer. The cell lysate is then centrifuged and passed into a second holding tank. Based on an estimated biofuel adsorption capacity in alkane (e.g., decane) of 16%, approximately half of the cell-free reaction fluid is pumped from the reactor to a decanting centrifuge each hour, in some embodiments. The gas phase is removed and the liquid phases separated. The organic phase, in some embodiments, is transferred to the distillation device for biofuel removal. The re-purified alkane is then cooled and injected with methane to produce a chilled methane-in-alkane foam for distributed entry back into the cell-free reactor. About 10% of the aqueous phase leaving the decanting centrifuge is removed to maintain a constant volume in the cell-free reactor and to remove any possible water soluble toxins. The aqueous catalyst stream is then cooled before single point entry into the bioreactor.

Cell Free Systems

The cell-free processes provided herein permit multiple enzymes to be expressed (e.g., from a bacterial artificial chromosome) during bacterial (e.g., *E. coli*) fermentation. In some embodiments, enzymes for the conversion of substrates (e.g., methane) to the desired chemical product (e.g., pyruvate) are expressed in a recombinant, typically rapidly-growing, bacterial strain (e.g., *E. coli*). Prior to cell harvest and lysis, the enzymes accumulate to optimal levels. Cell lysis enables periplasmically-expressed proteases (discussed below) to eliminate side pathways, shunting carbon to the product of interest. An optimized chemical environment activates respiration catalyzed by inner membrane vesicles formed during cell lysis, thereby providing a plentiful supply of ATP and removing excess reducing equivalents to recycle NAD+ and/or nicotinamide adenine dinucleotide phosphate (NADP+), if needed (see International Publication Numbers WO 2010/077806 and WO 2012/030980, incorporated by reference herein).

A "cell-free" composition, as used herein, refers to a composition substantially free of intact cells. One of skill in the art would understand that a certain percentage of the cells after lysing may be intact, e.g., less than 10%, less than 5%, less than 2%, less than 1%, or less than 0.5%. A "cell-free system," as used herein, is an isolated cell-free system containing a cell lysate or extract expressly engineered to include an enzyme or cascade of enzymes that, when acting in a given sequence (e.g., in an enzymatic pathway) and proportion over a determined substrate, results in the generation of a desired product (e.g., a biofuel or other chemical compound, or an intermediate thereto).

A "cell lysate," as used herein, refers to a fluid containing the contents of lysed cells. Cell lysates may be whole cell lysates and/or crude (unpurified) cell lysates. In some embodiments, cell lysates may be partially purified (e.g., to remove cellular debris/particulate such as damaged outer cell membranes). In some embodiments, cell lysates are prepared by high pressure lysis, thereby forming intracellular membrane vesicles that enable oxidative phosphorylation in the cell lysates. Other methods of preparing cell lysate are well-known in the art and include, without limitation, sonication, homogenization, enzymatic lysis using lysozyme, and freezing and grinding.

Sonication includes lysing cells by liquid shear and cavitation. DNA is also sheared during sonication, so it may not be necessary to add DNase to the cell suspension. Typically, the cell suspension is kept on ice to control temperature, and short pulses (5-10 sec) with pauses (10-30 sec) may be used to re-establish a low temperature.

Homogenizers may be used to press lyse cells by pressurizing the cell suspension and suddenly releasing the pressure. This creates a liquid shear capable of lysing cells. Multiple (2-3) passes are generally required to achieve adequate lysis. The high operating pressures, however, result in a rise in operating temperatures. Therefore, pressure cells may be cooled (4° C.) prior to use. In addition to temperature control, care should be taken to avoid inactivating proteins by foaming.

Enzymatic lysis is based on the digestion of the peptidoglycan layer of the bacterial cell wall by lysozyme. Gram-negative bacteria, however, have an outer membrane that is external to the cell wall and may need to be permeabilized to expose the peptidoglycan layer. Tris-buffered saline, often used as a buffer in lysis methods, effectively permeabilizes outer membranes. This effect can be enhanced by the addition of a chelating agent such as ethylenediaminetetraacetic acid (EDTA, e.g., 1 mM). EDTA chelates the magnesium ions that stabilize membranes. During cell lysis, DNA is liberated and it may be necessary to add DNase (1 mg/ml) to reduce the viscosity of the preparation. Enzymatic cell lysis can be carried out on any scale. To increase the level of cell lysis the solution may also be sonicated.

Another lysis method is to freeze the cells directly in liquid nitrogen and grind the frozen cells to a powder using a mortar and pestle that are chilled with liquid nitrogen. The powder can be stored indefinitely at −80° C., and the cell lysate can be prepared by adding the powder to buffer.

Cell lysates of methanotrophs and recombinant bacteria are combined in a cell-free system with at least one substrate, cofactor, or a combination thereof required for producing the desired biofuel or other chemical compound. "Substrate," as used herein, is a compound or mixture of compounds capable of providing the required elements needed to synthesize a compound of interest. In certain embodiments, a substrate may refer to a carbon source. In some embodiments, methane is the substrate.

"Cofactor," as used herein, is a non-protein chemical compound required for a protein's (e.g., enzyme's) biological activity. In some embodiments, cofactors are required for the cell-free biotransformation of methane to a biofuel or other chemical compound. Examples of cofactors include, without limitation, NADH, NAD+, ATP, ADP, Pi, and NADPH. In some embodiments, cofactors are provided by (e.g., present in) the cell extract.

Protease Targeting

Some aspects of the present disclosure use methods for silencing (e.g., eliminating or reducing) unwanted side reactions by inactivating one or more enzymes that is detrimental to a particular stage of the biotransformation process. In some embodiments, a detrimental enzyme is one that catalyzes a rate-limiting step in a biosynthetic pathway. This is achieved, in some embodiments, by engineering an enzyme to include a protease recognition site. Such recombinant enzymes typically have a protease recognition sequence selectively located in their primary amino acid sequence such that, despite the presence of the recognition sequence, the activity of the recombinant protein is sufficient to enable wild-type growth of the cell. The recombinant enzymes can be selectively inactivated by the introduction, expression, and/or activation of a cognate protease, which cleaves the recombinant target protein specifically at the protease recognition sequence, thereby rendering the recombinant enzyme inactive (or with reduced activity). The cognate protease is sequestered into a cellular compartment (e.g., periplasm) until inactivation of the recombinant enzyme is needed, at which time the protease is brought into contact with the recombinant enzyme to cleave and inactivate the enzyme.

The recombinant enzymes provided herein may be inactivated by any one of a variety of proteases that cleave at specific recognition sequences. As used herein, "protease recognition sequence," in the context of an enzyme, refers to an amino acid sequence that is recognized and cleaved by a cognate protease. In the context of a nucleic acid that encodes a protein, a "protease recognition sequence" refers to a sequence that encodes the amino acid sequence recognized and cleaved by a cognate protease. As used herein, "cognate protease" refers to a protease that cleaves and thereby inactivates a recombinant enzyme. Cognate proteases that may be used herein include those with a single, specific recognition sequence, meaning the proteases cleave within or adjacent to a specific sequence of one or more amino acids. In some embodiments, the proteins of the invention are prepared with an engineered human rhinovirus 3C protease recognition sequence.

Other examples of proteases that may be used in accordance with the invention include, without limitation, alanine carboxypeptidase, *Armillaria mellea astacin*, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB and Xaa-pro aminopeptidase (see Rawlings, S. D., et al., Handbook of Proteolytic Enzymes, Academic Press, 2013, Science, Elsevier Ltd., 4094 pages, incorporated herein by reference for its teachings relating to the structural chemistry and biological aspects of the proteases described therein). Other proteases may be used in accordance with the invention.

Compartmentalization of enzymes in either the cytoplasm or periplasm of bacteria (e.g., *E. coli*) provides an opportunity to overexpress components of biosynthetic pathways and to accumulate a specific protease without affecting cell health and growth. When the cells are lysed by, for example, scalable high pressure homogenizers, the intracellular compartments mix to activate the pathways and inactivate the deleterious enzymes; essentially to remodel the catalytic system. This permits the enzyme catalysts to be produced inexpensively, in some instances. Additionally, the absence of the cell wall and dispersion of the macromolecular catalysts throughout the entire reaction volume permits, in some embodiments, precise sampling for on-line monitoring as well as immediate dispersion of added substrates and reaction control reagents (e.g., affectors of pH, substrates). This enables, in some embodiments, the ability to approach complex biological conversions (e.g., converting methane to a biofuel) using technologies employed by traditional heterogeneous catalysis processes as described herein.

As discussed herein, some aspects of the invention relate to the inactivation of enzymes detrimental to biofuel (e.g., isobutanol) production. For example, in some embodiments, pyruvate dehydrogenase may be targeted by a protease in the manner described herein. Pyruvate dehydrogenase (E1) is the first component enzyme of pyruvate dehydrogenase complex (PDC). The pyruvate dehydrogenase complex contributes to transforming pyruvate into acetyl-CoA by a process called pyruvate decarboxylation. Acetyl-CoA may then be used in the citric acid cycle to carry out cellular respiration, thus pyruvate dehydrogenase contributes to linking the glycolysis metabolic pathway to the citric acid cycle and releasing energy via NADH.

In some embodiments, formaldehyde dehydrogenase may be targeted by a protease in the manner described herein. Formaldehyde dehydrogenase is an enzyme that catalyzes the chemical conversion of formaldehyde to formate.

Methanotrophs

Some aspects of the invention relate to enzymes that catalyze the conversion of methane to formaldehyde and are derived from a methanotroph. Enzymes are considered to be "derived from" an organism if they are expressed in that organism or obtained from that organism. Thus, in some embodiments, cell-free processes of the invention use cell extracts from methanotrophs (e.g., *Methylococcus capsulatus* Bath) to provide methane monooxygenase, a biological catalyst for methane activation. "Methanotrophs," as used herein, refers to prokaryotes that are able to metabolize methane as their only source of carbon and energy. Methanotrophs can grow aerobically or anaerobically and require single-carbon compounds to survive.

In some embodiments, factors to consider when using methanotrophs for the conversion of methane to a biofuel or other chemical compound, include without limitation: methanotrophic culture densities on the order of 5-15 grams cell dry weight per liter (e.g., 10 grams cell dry weight per liter) or 25-100 grams dry weight per liter (e.g., 50 grams dry weight per liter grams dry weight per liter within 2-5 years (e.g., 2.5 years); a turnover frequency of methane oxidation by the methane monooxygenase on the order of 25 to 75 50 $\sec^{-1}$ (e.g., 50 $\sec^{-1}$) and an effective catalyst lifetime of 10 to 30 hours; net zero consumption of reducing equivalents in the oxidation of methane to precursor compounds for biofuel production and protease targeting of side processes to ensure maximum carbon flux from methane to a biofuel or other chemical compound.

In some embodiments, batch culture systems and/or continuous culture systems are used to systematically manipulate growth conditions, e.g., varying nitrogen, phosphorous, iron, copper, and temperature, along with the addition of paraffin (Han B, et al. 2009 *Appl Microbiol Biotechnol* 83:669-77) to stimulate both high growth rates and cell densities in methanotrophs (e.g., *M. capsulatus* Bath). Thus, in some embodiments, any one or more of nitrogen, phosphorous, iron, copper, and paraffin may be used in the cell-free process of the invention to improve methanotroph growth rates and to improve the accumulation of MMO.

In some embodiments, the genome of the methanotrophs is modified to have enhanced pMMO expression and activity.

Recombinant Bacteria

Some aspects of the invention relate to enzymes that catalyze the conversion of formaldehyde to a biofuel or other chemical compound and which are derived from recombinant bacteria. As used herein, "recombinant bacteria," or a "recombinant cell," refers to a cell into which a foreign, or exogenous, nucleic acid (i.e., nucleic acid not native to the cell) is introduced. A recombinant cell may include a recombinant nucleic acid (e.g., DNA or RNA), which is formed artificially by combining nucleic acids from different sources. In some embodiments, the foreign nucleic acid is integrated into the genome of the cell, whereas in other embodiments, the foreign nucleic acid is not integrated into the genome of the cell. The terms "recombinant cell" and "genetically engineered cell" may be used interchangeably herein.

While many of the embodiments provided herein describe the use of recombinant *Escherichia coli* (*E. coli*), it should be understood that the invention is not so limited, but rather contemplates the use of any bacterial cells that grow rapidly and can be easily genetically manipulated. Thus, methods associated with the present disclosure encompass lysates from any type of cell, e.g., prokaryotic and eukaryotic cells. In some embodiments, the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other non-limiting examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., *Pectobacterium* spp., and *Trichoderma* spp. In some embodiments, the cell is an algal cell, a plant cell, an insect cell, or a mammalian cell. It should be appreciated that some cells compatible with the invention may express an endogenous copy of one or more of the genes associated with the invention as well as a recombinant copy. It should also be appreciated that some cells for use in accordance with the invention do not contain the wild-type chromosomal copy of a gene encoding the wild-type enzyme (e.g., the wild-type enzyme corresponding to the genetically-engineered enzyme introduced into the cell).

In some embodiments, *E. coli* cells are used as they are economical, well studied, and amenable to genetic manipulation. In some embodiments, yeast cells are used.

In some embodiments, the cell lysate that contains enzymes that catalyze the conversion of formaldehyde to a biofuel or other chemical compound is a lysate of a recombinant *E. coli* cell engineered to overexpress one or more enzymes described herein. In some embodiments, the cell lysate is a lysate of an *E. coli* cell engineered to overexpress a group of enzymes, e.g., two, three, four, five, six, seven, eight, nine, ten, eleven, twelve, thirteen, fourteen, fifteen, sixteen, seventeen, eighteen, nineteen, twenty, or more than twenty enzymes. In some embodiments, the cell lysate is a combination of different cell lysates, e.g., a combination of two, three, four, five, six, seven, eight, nine, ten, or more than ten different cell lysates, obtained from two, three, four, five, six, seven, eight, nine, ten, or more than ten different cells, e.g., from different organisms, each engineered to overexpress one or more enzymes that the conversion of formaldehyde to a biofuel or chemical compound. In some embodiments, lysates from different organisms (e.g., different strains of bacteria) are combined. In some embodiments, different engineered *E. coli* strains (e.g., overexpressing different production pathway proteins) are combined to optimize enzyme levels prior to creating a single engineered strain with all overexpressed proteins.

The cells provided herein, in some embodiments, are prokaryotic cells that may be transformed with nucleic acids encoding as enzymes as provided herein. Transformation and transfection are processes by which exogenous genetic material is introduced into a prokaryotic cell and into a eukaryotic cell, respectively. Transformation can be achieved by electroporation or by chemical means. The cells to be transformed are typically in a state of competence. Thus, in some embodiments, the cells provided herein are electrocompetent or chemically competent cells (see, e.g., Donahue et al. *Focus* 20, 1998, (2):54-56; Donahue et al. *Focus* 20, 1998, (2):77-78' Inoue et al. *Gene* 96, 1990, (1): 23-28, each of which is incorporated by reference herein). A variety of electrocompetent and chemically competent cells are known in the art and may be used in accordance with the invention.

Cells, in some embodiments, may comprise selectable markers. Selectable markers include, without limitation, genes encoding proteins that increase or decrease either resistance or sensitivity to antibiotics (e.g., ampicillin resistance genes, kanamycin resistance genes, neomycin resistance genes, tetracyclin resistance genes and chloramphenicol resistance genes) or other compounds, genes encoding enzymes with activities detectable by standard assays known in the art (e.g., β-galactosidase, luciferase or alkaline phosphatase), and genes that visibly affect the phenotype of transformed or transfected cells, hosts, colonies, or plaques (e.g., green fluorescent protein). Other selectable markers known in the art may also be used in accordance with the invention.

A "nucleic acid," as used herein, refers to a polymer of at least three nucleotides (e.g., adenine, thymine, cytosine, guanine, uracil) covalently linked together. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages). A nucleic acid of the present disclosure will generally contain phosphodiester bonds. A nucleic acid may be single-stranded (ss) or double-stranded (ds), DNA or RNA. In some embodiments, a nucleic acid is in the form of cDNA. In some embodiments, a nucleic acid is in the form of genomic DNA. Nucleic acids of the present disclosure may be in the form of vectors including, without limitation, plasmids, cosmids, and artificial chromosomes (e.g., bacterial artificial chromosomes (BACs) and yeast artificial chromosomes (YACs)). Other nucleic acid-based vectors are described below.

The nucleic acids used herein, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., Molecular Cloning: A Laboratory Manual (2nd ed.), Vols. 1-3, Cold Spring Harbor Laboratory, (1989); Current Protocols In Molecular Biology, Ausubel, ed. John Wiley & Sons, Inc., New York (1997); Laboratory Techniques In Biochemistry And Molecular Biology: Hybridization With Nucleic Acid Probes, Part I. Theory and Nucleic Acid Preparation, Tijssen, ed. Elsevier, N.Y. (1993), incorporated by reference herein.

Alternatively, these nucleic acids can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066, incorporated by reference herein.

Nucleic acids encoding enzymes of the present disclosure may comprise regulatory sequences operably linked to coding sequences. As used herein, a regulatory sequence (e.g., promoter sequence) and a coding sequence are said to be "operably" linked when they are covalently linked in such a way as to place the expression or transcription of the coding sequence under the influence or control of the regulatory sequences (e.g., such that the regulatory sequence "drives" transcriptional initiation and/or expression of the coding sequence). For example, for a coding sequences that is to be translated into a functional enzyme, two DNA sequences are considered operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into the enzyme. Thus, a promoter region would be operably linked to a coding sequence if the promoter region can effect transcription of that DNA sequence such that the resulting transcript can be translated into the desired enzyme.

When a nucleic acid that encodes any of the enzymes provided herein is expressed in a cell, a variety of transcription control sequences may be used to direct its expression. For example, a nucleic acid may contain a promoter, an enhancer, and/or a terminator. Alternatively, the vector into which the nucleic acid is inserted may contain such regulatory sequences. A "promoter," as used herein, refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive (e.g., unregulated), inducible, activatable, repressible, tissue-specific or any combination thereof. A promoter drives expression or drives transcription of the nucleic acid sequence that it regulates. A promoter may be one naturally associated with a gene or sequence, as may be obtained by isolating the 5'-non-coding sequences located upstream of the coding segment and/or exon of a given gene or sequence. Such a promoter can be referred to as "endogenous" or "native." A coding nucleic acid segment, in some embodiments may be positioned under the control of a recombinant or heterologous promoter, which refers to a promoter that is not normally associated with the encoded nucleic acid sequence in its natural environment. Such promoters may include promoters of other genes, promoters isolated from any other prokaryotic, viral or eukaryotic cell, and synthetic promoters that are not "naturally occurring" such as, for example, those that contain different elements of different transcriptional regulatory regions and/or mutations that alter expression through methods of genetic engineering that are known in the art. In addition to producing nucleic acid sequences of promoters synthetically, sequences may be produced using recombinant cloning and/or nucleic acid amplification technology, including polymerase chain reaction (PCR).

Promoters suitable for use with prokaryotic hosts include, without limitation, the β-lactamase and lactose promoter systems, alkaline phosphatase, a tryptophan (trp) promoter system, and numerous hybrid promoters such as the tac promoter. However, other known bacterial promoters are also suitable, e.g., the lad promoter, the T3 promoter, the T7 promoter, the arabinose promoter, the gpt promoter, the lambda PR promoter, the lambda PL promoter, promoters from operons encoding glycolytic enzymes such as 3-phosphoglycerate kinase (PGK), and the acid phosphatase promoter. Their nucleotide sequences have been published, thereby enabling a skilled worker operably to ligate them to a sequence of interest using linkers or adaptors. Promoters for use in bacterial systems also will contain a Shine-Dalgarno (S.D.) sequence operably linked to the coding sequence. In some embodiments, the host cell may be modified genetically to adjust concentrations of metabolite or inducer transporter proteins so that all cells in a culture will be induced equivalently.

Promoters suitable for eukaryotic cells, e.g., yeast cells, are also known in the art. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoting sequences for use with yeast hosts include, without limitation, promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose phosphate isomerase, phosphoglucose isomerase, and glucokinase.

An "inducible promoter," as used herein, is one that is characterized by initiating or enhancing transcriptional activity when in the presence of, influenced by or contacted by an inducer or inducing agent. An "inducer" or "inducing agent" may be endogenous or a normally exogenous compound or protein that is administered in such a way as to be active in inducing transcriptional activity from the inducible promoter. Inducible promoters for use in accordance with the invention include any inducible promoter described herein or known to one of ordinary skill in the art. Examples of inducible promoters include, without limitation, chemically/biochemically-regulated and physically-regulated promoters such as isopropyl β-D-1-thiogalactopyranoside (IPTG)-regulated promoters, alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells). Other inducible promoters may be used in accordance with the invention.

A "codon," as used herein, refers to a set of three adjacent nucleotides that encode an amino acid. In some embodiments, nucleic acids are codon-optimized for improved expression of the genetically engineered enzymes useful in the present invention. Codon optimization, also referred to as biased codon usage, refers to differences in the frequency of occurrence of synonymous codons in coding DNA.

"Isozymes," as used herein, refer to enzymes that differs in amino acid sequence but catalyzes the same chemical reaction or produces the same reaction product from starting material.

Enzymes of the present disclosure may, in some embodiments, be expressed episomally. Thus, the present disclosure contemplates the use of vectors comprising a nucleic acid that express enzymes as described herein. A "vector," as used herein, may be any of a number of nucleic acids into which a desired sequence or sequences may be inserted by restriction and ligation for transport between different genetic environments or for expression in a cell. Vectors are typically composed of DNA although RNA vectors are also available. Examples of vectors in accordance with the present disclosure include, without limitation, plasmids, cosmids, fosmids, phagemids, virus genomes, and artificial chromosomes (e.g., BACs, YACs). In some embodiments, a nucleic acid of the present disclosure is provided in a recombinant cloning vector. In some embodiments, a nucleic acid variant is expressed in a recombinant expression vector.

A cloning vector of the present disclosure is able to replicate autonomously or integrated in the genome of a cell. A cloning vector has an endonuclease restriction sequence at which the vector may be cut in a determinable fashion and into which a desired DNA sequence may be ligated such that the new recombinant vector retains its ability to replicate in a cell. In the case of plasmids, replication of the desired sequence may occur many times as the plasmid increases in copy number within a cell such as a bacterium or just a single time per cell before the cell reproduces by mitosis. An expression vector of the present disclosure is one into which a desired DNA coding sequence may be inserted by restriction and ligation such that it is operably linked to regulatory sequences and may be expressed as an RNA transcript.

Vectors of the invention may further comprise a marker sequence for use in the identification of cells that have or have not been transformed or transfected with the vector. Markers include, for example, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., β-galactosidase, luciferase or alkaline phosphatase), and genes that visibly affect the phenotype of transformed or transfected cells, hosts, colonies or plaques (e.g., green fluorescent protein). In some embodiments, the vectors used herein are capable of autonomous replication and expression of the structural gene products present in the DNA segments to which they are operably linked.

The nucleic acids encoding enzymes associated with the present disclosure can be obtained from a variety of sources. As one of ordinary skill in the art would be aware, homologous genes for these enzymes exist in many species and can be identified by homology searches, for example, through using the internet-based Basic Local Alignment Search Tool (BLAST) made available by the National Center for Biotechnology Information (NCBI). Nucleic acids encoding these enzymes can be amplified by polymerase chain reaction (PCR) from DNA from any source which contains the given enzyme, for example, using degenerate primers, as would be understood by one of ordinary skill in the art. In some embodiments, nucleic acids encoding a given enzyme can be synthetic. Any means of obtaining nucleic acids encoding the enzymes discussed herein are compatible with aspects of the present disclosure.

Expression of the enzymes of the present disclosure may be determined using routine methods known to those of ordinary skill in the art. These methods include, but are not limited to, direct RNA amplification, reverse transcription of RNA to cDNA, real-time RT-PCR, amplification of cDNA, hybridization, and immunologically based assay methods, which include, but are not limited to Western blotting, immunohistochemistry, antibody sandwich capture assay, ELISA, and enzyme-linked immunospot assay (EliSpot assay). For example, the determination of the presence of levels of nucleic acid molecules of the invention in a sample such as a tissue or cell lysate can be carried out via any standard nucleic acid determination assay, including PCR, or assaying with labeled hybridization probes. Such hybridization methods include, but are not limited to, microarray techniques.

The present disclosure thus involves, in one aspect, methods involving enzymes, nucleic acids encoding those enzymes, functional modifications and variants of the foregoing, as well as uses relating thereto. Homologs and alleles of the nucleic acids described herein can be identified by conventional techniques (see, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

Aspects of the present disclosure relate to the expression of one or more enzymes in a genetically engineered cell followed by cell lysis. In some embodiments, one or more enzymes are expressed and optionally sequestered in the cytoplasm of a cell prior to lysis. In some embodiments, one or more enzymes are expressed and optionally sequestered in the periplasmic space. Sequestration of enzymes in the periplasmic space is known in the art, see, e.g., PCT Application No. PCT/US2011/035639, incorporated herein by reference. Upon lysis of a cell to provide a cell lysate, the sequestered enzymes are free to react with one or more substrates also present in the lysate or different lysate.

Cell-Free Biotransformation of Methane to Biofuel and Other Chemical Compounds

The cell-free biosynthetic system provided herein is useful for producing a biofuel or other chemical compound (e.g., pyruvate) from methane. For example, isobutanol of relatively high purity (99%), suitable for use as a second-generation biofuel, can be produced from methane in accordance with the invention. Isobutanol has several properties which make it ideal as a replacement for gasoline: its energy density is 98% that of gasoline, it does not readily absorb water (unlike ethanol), thereby avoiding corrosion of engine parts, and it can be combined with gasoline in any proportion, permitting it to be "dropped-in" to the current combustible infrastructure. Isobutanol derived from natural gas can be combined with conventional gasoline for rapid commercialization, or it can be used as a full replacement of oil-derived fuel, depending on economic performance of the process and global oil prices.

Enzymes that catalyze the conversion of methane to formaldehyde include, without limitation, methane monooxygenase (catalyzes methane to methanol) and methanol dehydrogenase (catalyzes methanol to formaldehyde). In some embodiments, methane monooxygenase and methanol dehydrogenase are provided in one or more cell lysate(s) obtained from methanotrophs. In other embodiments, methane monooxygenase is provided in a cell lysate obtained from methanotrophs, while methanol dehydrogenase is provided in a cell lysate from recombinant bacteria, such as, for example, *Escherichia coli*. The invention also contemplates providing methane monooxygenase and/or methanol dehydrogenase exogenously in, for example, purified or partially purified form.

Enzymes that catalyze the conversion of formaldehyde to pyruvate include, without limitation, hexulose-6-phosphate synthase, 6-phospho-3-hexuloisomerase, 6-phosphofructokinase, fructose biphosphate aldolase, triose phosphate isomerase, transketolase, ribose-5-phosphate isomerase, ribose-5-phosphate 3-epimerase, glyceraldehyde 3-phosphate dehydrogenase, phosphoglycerate kinase, phosphoglycerate mutase, enolase, and pyruvate kinase.

Enzymes that catalyze the conversion of pyruvate to isobutanol include, without limitation, acetolactate synthase, acetohydroxy acid isomeroreductase, dihydroxy acid dehydratase, alpha-ketoisovalerate decarboxylase, and isobutanol dehydrogenase.

Enzymes for use in accordance with the invention are shown in Table I.

TABLE I

| Substrate(s) | Product(s) | Enzyme | EC number(s) |
|---|---|---|---|
| methane | methanol | methane monooxygenase | 1.14.13.25, 1.14.18.3 |
| methanol | formaldehyde | methanol dehydrogenase | 1.1.1.244, 1.1.2.7, 1.1.99.37 |
| formaldehyde, D-ribulose 5-phosphate | hexulose 6-phosphate | hexulose-6-phosphate synthase | 4.1.2.43 |
| hexulose 6-phosphate | beta-D-fructofuranose 6-phosphate | 6-phospho-3-hexuloisomerase | 5.3.1.27 |
| beta-D-fructofuranose 6-phosphate | fructose-1,6-bisphosphate | 6-phosphofructokinase | 2.7.1.11 |
| fructose-1,6-bisphosphate | D-glyceraldehyde 3-phosphate, dihydroxyacetone phosphate | fructose bisphosphate aldolase | 4.1.2.13 |
| dihydroxyacetone phosphate | D-glyceraldehyde 3-phosphate | triose phosphate isomerase | 5.3.1.1 |
| D-glyceraldehyde 3-phosphate, beta-D-fructofuranose 6-phosphate | D-erythrose 4-phosphate, D-xylulose 5-phosphate | transketolase | 2.2.1.1 |
| D-erythrose 4-phosphate, beta-D-fructofuranose 6-phosphate | D-glyceraldehyde 3-phosphate, D-sedoheptulose 7-phosphate | transaldolase | 2.2.1.2 |
| D-glyceraldehyde 3-phosphate, D-sedoheptulose 7-phosphate | D-ribose 5-phosphate, D-xylulose 5-phosphate | transketolase | 2.2.1.1 |
| D-ribose 5-phosphate | D-ribulose 5-phosphate | ribose-5-phosphate isomerase | 5.3.1.6 |
| D-xylulose 5-phosphate | D-ribulose 5-phosphate | ribulose-5-phosphate 3-epimerase | 5.1.3.1 |
| D-glyceraldehyde 3-phosphate | 1,3-bisphospho-D-glycerate | glyceraldehyde 3-phosphate dehydrogenase | 1.2.1.12 |
| 1,3-bisphospho-D-glycerate | 3-phospho-D-glycerate | phosphoglycerate kinase | 2.7.2.3 |
| 3-phospho-D-glycerate | 2-phospho-D-glycerate | phosphoglycerate mutase | 5.4.2.11/5.4.2.12 |
| 2-phospho-D-glycerate | phosphoenolpyruvate | enolase | 4.2.1.11 |
| phosphoenolpyruvate | pyruvate | pyruvate kinase | 2.7.1.40 |
| 2 pyruvate | (S)-2-acetolactate | acetolactate synthase | 2.2.1.6 |
| (S)-2-acetolactate | 2,3-dihydroxy-3-methylbutanoate | acetohydroxy acid isomeroreductase | 1.1.1.86 |

TABLE I-continued

| Substrate(s) | Product(s) | Enzyme | EC number(s) |
| --- | --- | --- | --- |
| 2,3-dihydroxy-3-methylbutanoate | 3-methyl-2-oxobutanoate | dihydroxy acid dehydratase | 4.2.1.9 |
| 3-methyl-2-oxobutanoate | isobutanal | alpha-ketoisovalerate decarboxylase | 4.1.1.72 |
| isobutanal | isobutanol | isobutanol dehydrogenase | 1.1.1.1 |

It should be understood that any one or more of the enzymes provided herein may be used in any one or more cell lysates of a cell-free biosynthesis process of the invention. The invention also contemplates the use of one or more cell lysates, each containing, for example, a different combination of enzymes that convert a substrate (e.g., methane) to a product (e.g., isobutanol) or product intermediate (e.g., formaldehyde or pyruvate).

Figure 5:
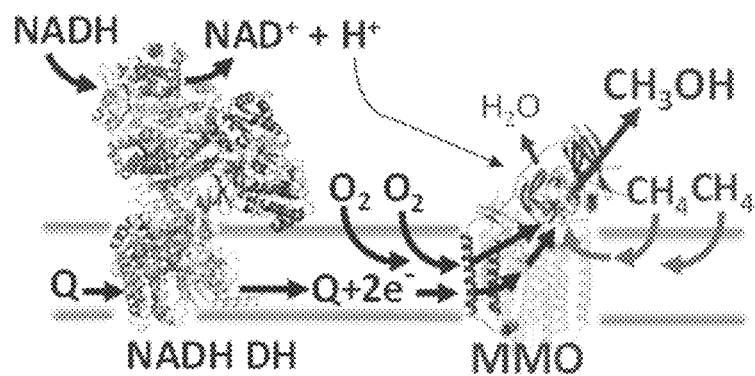
FIG. 5 shows a diagram of the methane monooxygenase (MMO) catalytic system assuming that adequate NADH is supplied by a nicotinamide adenine dinucleotide (NAD+)-coupled methanol dehydrogenase.
Figure 6:
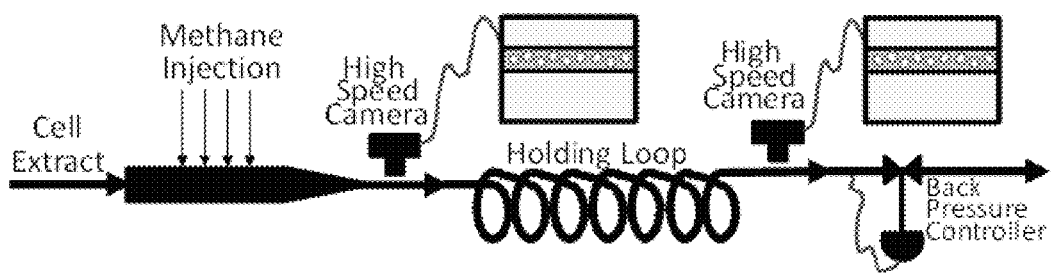
FIG. 6 shows a diagram of an apparatus for use in some embodiments to assess gas/liquid interface formation and stability.

An example of a biosynthetic pathway for cell-free conversion of methane to isobutanol in accordance with the invention is depicted in FIG. 5. The cell-free approach provided herein, which combines cell extracts from at least two different bacterial cells, including a methanotroph (e.g., *Methylococcus capsulatus* Bath), minimizes the issues associated with engineering a single organism with all of the enzymes necessary for conversion of methane to biofuel. Nonetheless, in some embodiments, a single organism may be used to express all enzymes necessary for the conversion of methane to a biofuel or other chemical compound. In the example depicted in FIG. 5, cell lysates from *M. capsulatus* Bath cells and from *E. coli* cells are used. The first step, conversion of methane to methanol, is catalyzed by the methane monooxygenase (MMO) provided in the lysate of the methanotroph. The second step, conversion of methanol to formaldehyde, is catalyzed by a heterologous (e.g., from different species) NAD-linked methanol dehydrogenase (e.g., from *Bacillus methanolicus*, de Vries G E, et al. 1992 *J Bacteriol* 174:5346-53, incorporated by reference herein), which replaces methanol dehydrogenase native to the methanotroph. This NAD-linked methanol dehydrogenase provides the necessary NADH reductant for the methane monooxygenase, resulting in a net zero consumption of electrons for conversion of methane to formaldehyde. Thus, in some embodiments, methanotrophs of a cell-free system of the invention may express methane monooxygenase and an exogenous, or recombinant, NAD-linked methanol dehydrogenase.

In native methanotroph metabolism, formaldehyde is further oxidized by formaldehyde dehydrogenase to formate, then to $CO_2$ to generate energy for methanotroph cell function. This is a limitation in the use of intact methanotrophs for bioproduction. Because only MMO and methanol dehydrogenase from the methanotroph are typically used in the cell-free process of the invention, this carbon route, in some embodiments, can be eliminated without affecting methanotroph function by targeting the formaldehyde dehydrogenase for cleavage by a protease expressed in recombinant bacterial (e.g., *E. coli*) cells.

In some embodiments, the NAD-linked methanol dehydrogenase is not expressed in the methanotroph but rather in another bacterial cell, such as *E. coli*, as discussed herein.

Additional steps depicted in FIG. 5 for the conversion of formaldehyde to isobutanol are catalyzed by enzymes provided in an extract of another recombinant cell(s) (e.g., *E. coli*). Two ribulose monophosphate cycle enzymes, hexulose-6-phosphate synthase and 6-phospho-3-hexuloisomerase, are overexpressed in the cell(s) along with a ketoisovalerate decarboxylase and an isobutanol oxidoreductase, which are required for the conversion of pyruvate to isobutanol. In addition to eliminating further oxidation of formaldehyde to $CO_2$, protease targeting methods may be used in certain embodiments to eliminate flux from pyruvate to other molecules by targeting pyruvate dehydrogenase for cleavage by a protease. Thus, in some embodiments, recombinant bacteria of the cell-free system of the invention may express any one or more of hexulose-6-phosphate synthase, 6-phospho-3-hexuloisomerase, ketoisovalerate decarboxylase, and isobutanol oxidoreductase. In some embodiments, the recombinant bacteria may also express a protease that targets an engineered formaldehyde dehydrogenase and/or a pyruvate dehydrogenase. In some embodiments, a protease may be added exogenously.

Delivering methane and oxygen to the methane monooxygenase may be accomplished by first diffusing the gases into the water phase, in some embodiments. By removing the cell wall barrier that has to be traversed in a living cell, the cell-free process provided herein simplifies the mass transfer process. In one embodiment, the gases are fed separately into a reactor in order to avoid gas mixing until they have entered the aqueous phase, thereby avoiding problems associated with spontaneous combustion. An example of a stable multiphase system is depicted in FIG. 1. This diagram includes the decane phase, which is used to help deliver the methane and to absorb the isobutanol as it is being produced. Small bubbles of methane are introduced into the decane phase before it enters the cell-free reactor. Methane has much higher solubility in decane than in water, thus the decane surface area in contact with the aqueous phase helps to diffuse the methane into the aqueous phase. Nonetheless, in some embodiments, some of the methane gas is injected directly into the aqueous phase.

Figure 7:
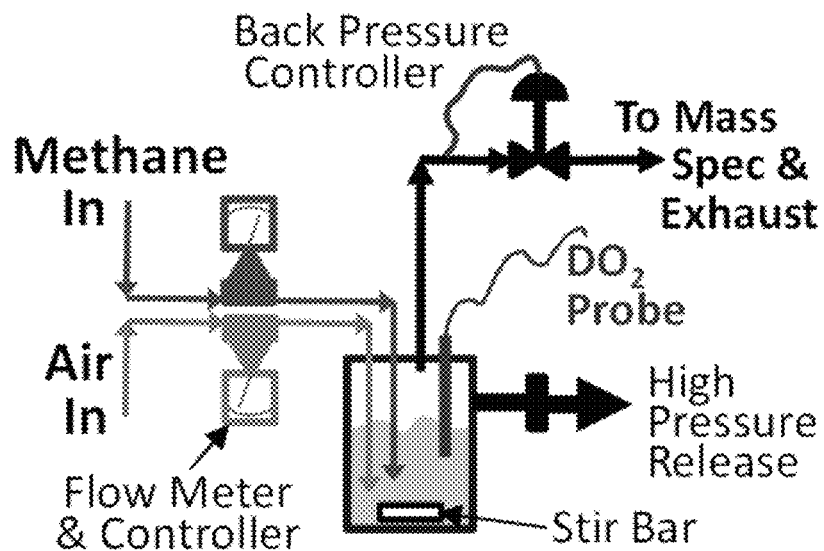
FIG. 7 shows a diagram of an apparatus for use in some embodiments to assess system performance and safety.

To assess the formation and stability of the gas/liquid and liquid/liquid interfaces, for example, the formation and stability of methane gas bubbles, the apparatus depicted in FIG. 7 may be used in some embodiments. Methane may be injected into the cell extract solution as it flows past the injection nozzles. An initial high speed camera permits accurate measurement of the size and uniformity of the bubbles formed. This fluid then passes into a holding loop and, after a set interval, is monitored by a second high speed camera to measure the stability of the gas bubbles. In some embodiments, the incubation time after bubble formation is adjusted by changing the size of the holding loop and/or the flow rate. The apparatus depicted in FIG. 7 may also be used to examine the effects of nozzle design and injection pressure as well as the effect of multiple nozzles on bubble size and stability.

In some embodiments, fatty acids and/or surfactants are used to help form and stabilize the gas/liquid interface. Without being bound by theory, the hydrophobic tails and hydrophilic carboxylic acid heads of fatty acids cause them to collect at the gas/liquid interface to stabilize it.

In some embodiments, methane gas bubbles produced are smaller than 3 µm to 7 µm in diameter. For example, the methane gas bubbles produced may be smaller than 3 μm, 4 μm, 5 μm, 6 μm, or 7 μm in diameter. In some embodiments, the methane gas bubbles remain smaller than 8 μm to 12 μm in diameter for a certain period of time after initial bubble formation. For example, the methane gas bubbles may remain smaller than 8 μm, 9 μm, 10 μm, 11 μm, or 12 μm for at least one, two, three, four or five minutes after initial bubble formation.

Further, the apparatus depicted in FIG. 7 may be used to study the formation and stability of methane in decane foam as well as the formation of the emulsion diagrammed in FIG. 1. As discussed above, surface active agents may be used to help form and stabilize the desired interfaces that define the methane bubbles in the decane phase as well as the decane droplets in the cell-free reactor emulsion.

Figure 8:
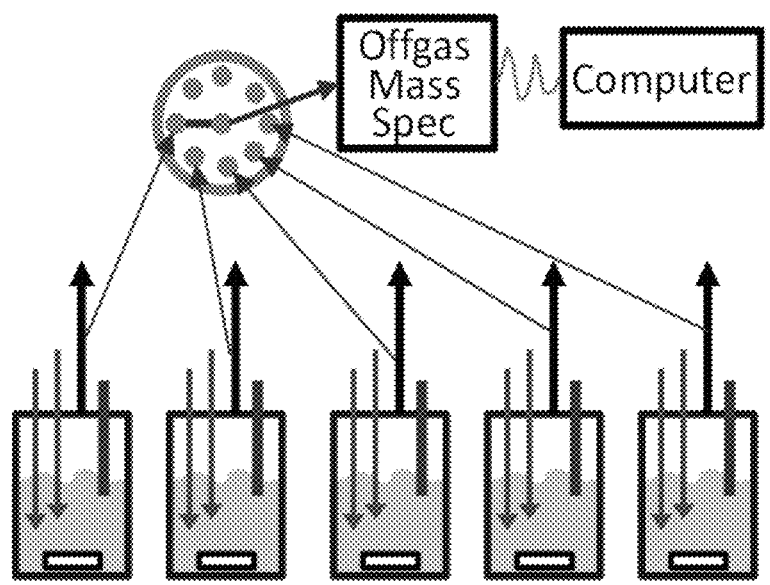
FIG. 8 shows a diagram of multiplexed instrumented reactors for use in assessing MMO activity and methanotroph cell growth.

To assess the safety and productivity of the cell-free biotransformation processes of the invention, the apparatus shown in FIG. 8 may be used in some embodiments. This reactor permits separate adjustment of methane and air injection rates and pressures. These vessels are typically small with working volumes of 10 to 100 ml, which helps to conserve extract and to minimize safety risks. The back pressure is controlled, and temperature and dissolved oxygen monitored. The cooling/heating loop is not shown in the reactor depicted in FIG. 8. Such reactors may be insulated to permit calculation of heat balance by monitoring the flow rate and temperature rise (or decrease) of the cooling/heating fluid. Further, the entering gases flow rates may be recorded and the off-gas composition may be monitored by an exit gas mass spec such that material balances indicate methane and oxygen utilization rates. Liquid samples may be analyzed by HPLC or a separate mass spec to indicate accumulation of intermediates and products. These values may be compared with measured heat evolution rates to provide confidence for performance assessments.

In some embodiments, the apparatus shown in FIG. 8 may be used without the decane phase to provide an initial assessment of any safety limits related to possible gas mixing. As confidence is gained and safety demonstrated, decane alone may be introduced to form an emulsion. In some embodiments, decane/methane foams may be injected to fully replicate the final system.

Figure 9:
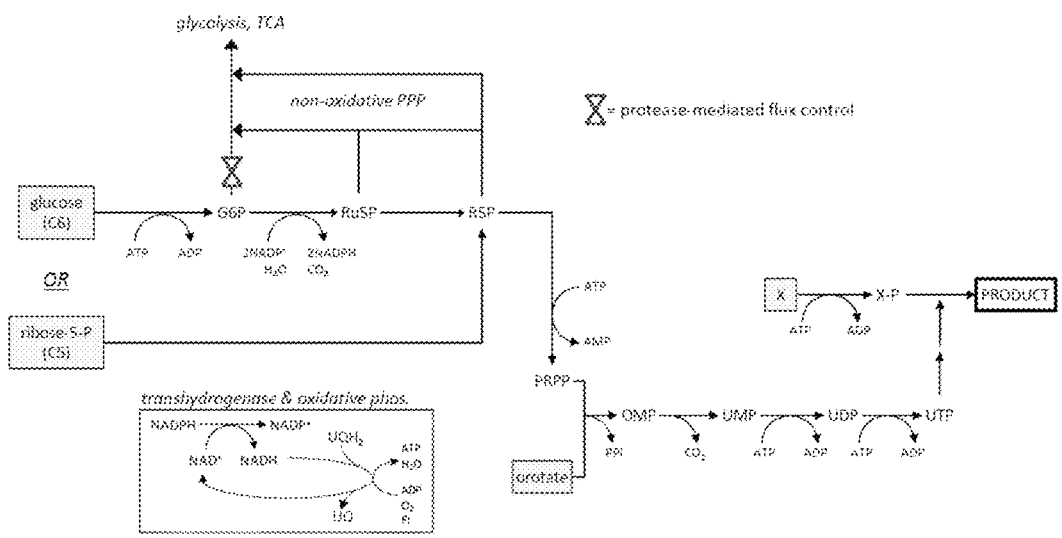
FIG. 9 shows a diagram demonstrating feedstock flexibility.
Figure 10:
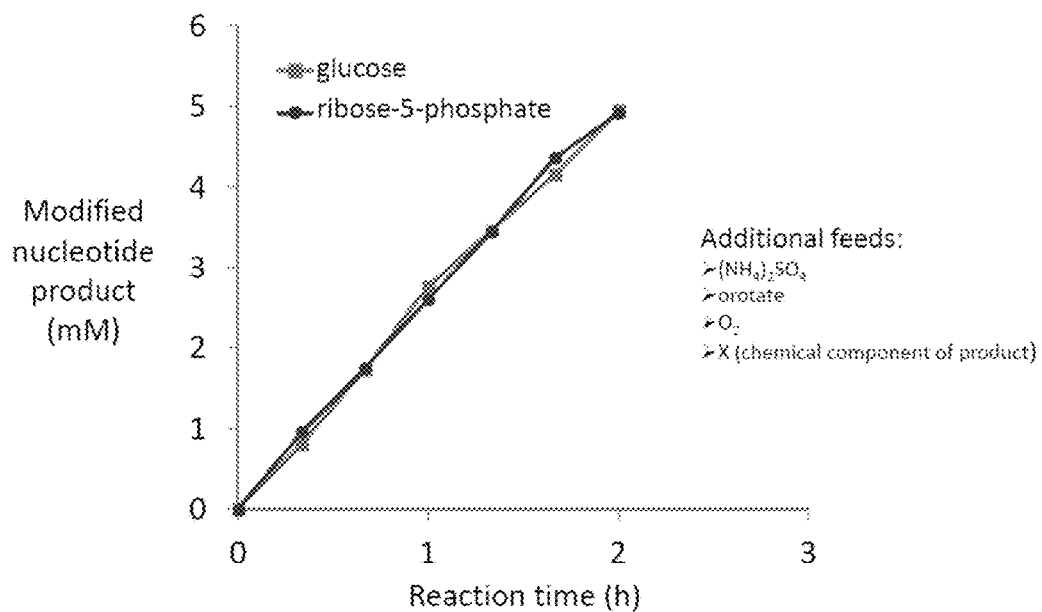
FIG. 10 shows a graph of data demonstrating that a single extract can accept glucose or ribose-5-P.
Figure 11:
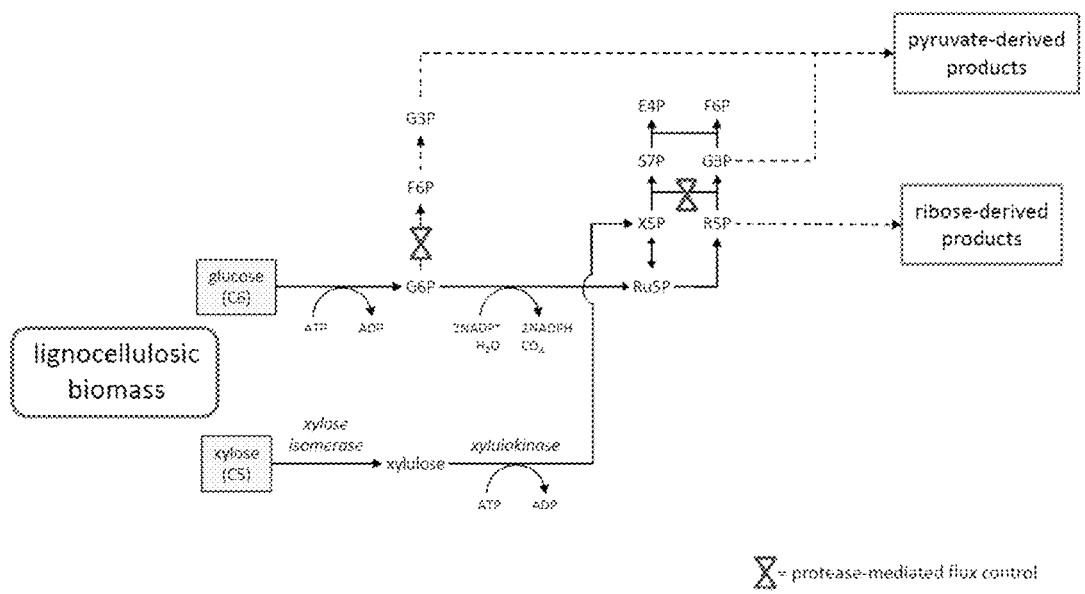
FIG. 11 shows a diagram demonstrating use of 5-carbon (C5) and 6-carbon (C6) sugars in cell-free reactions.
Figure 12:
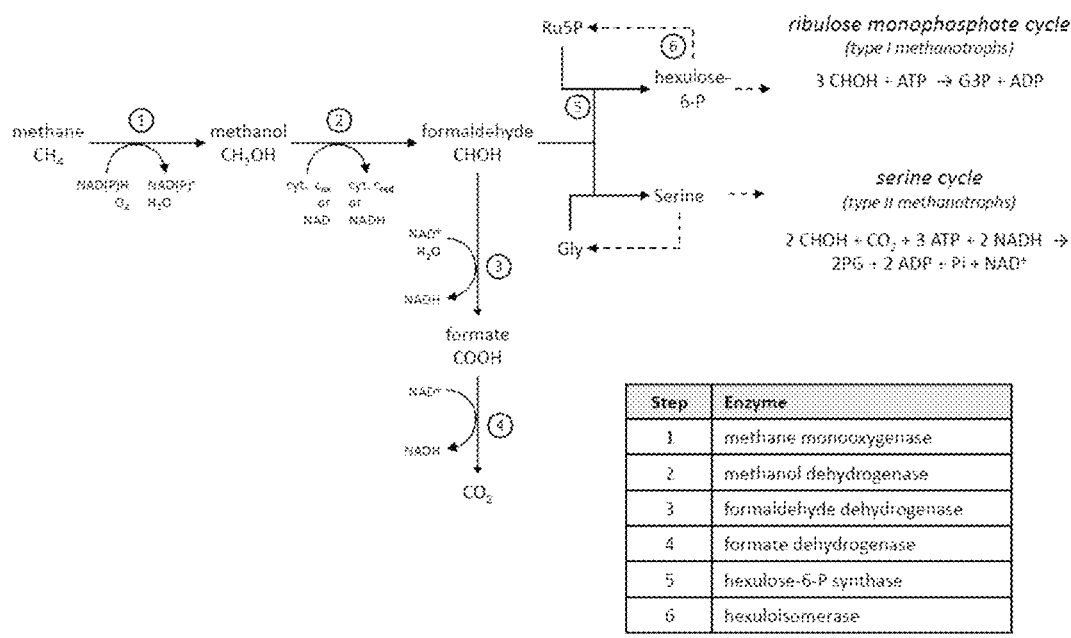
FIG. 12 shows a diagram of methane metabolism.
Figure 13:
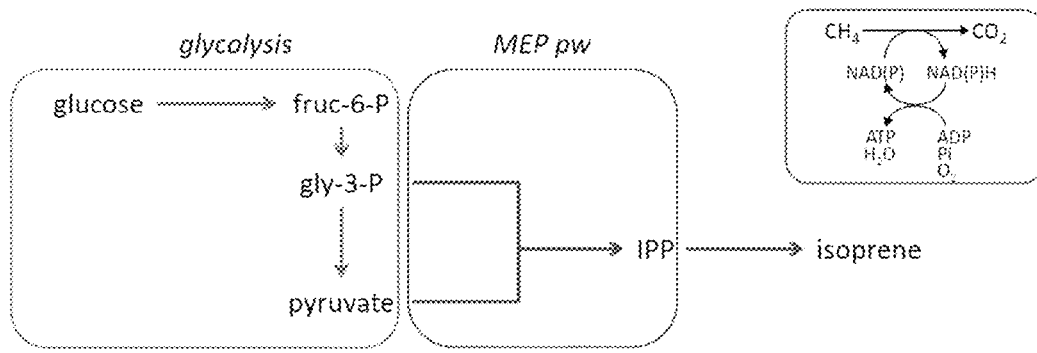
FIG. 13 shows a diagram of the isoprene pathway, requiring energy and reducing equivalents.
Figure 14:
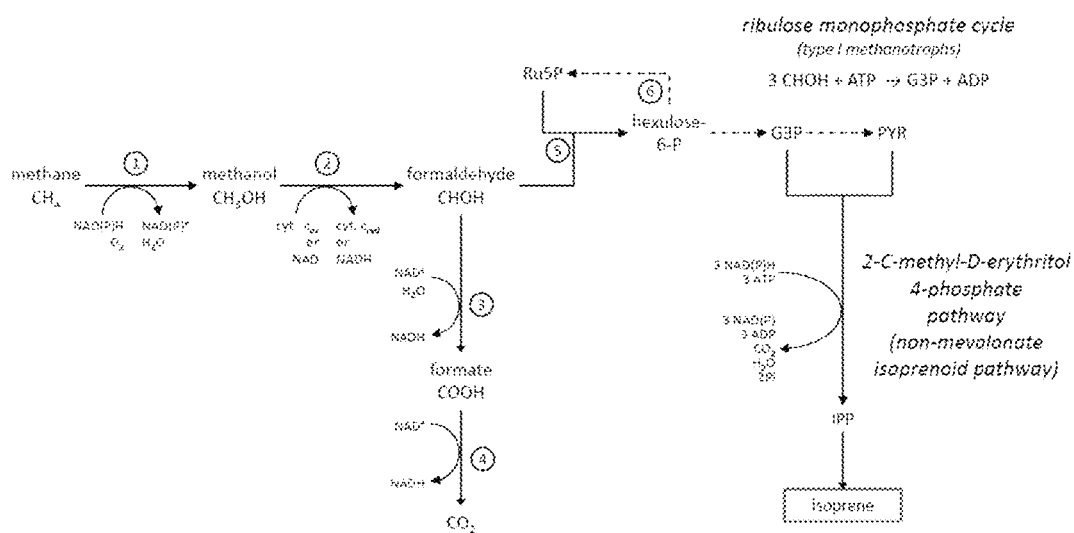
FIG. 14 shows a diagram of methane as the sole carbon source for isoprene.

In other embodiments, the apparatus shown in FIG. 8 may be used to assess MMO activities and methanotroph growth. In yet other embodiments, a multiplexed reactor system, as shown in FIG. 9, may be used to measure MMO activity and cell extract performance under working conditions to improve relevant performance characteristics and longevities.

In addition, in some embodiments, it may be economically advantageous to grow the methanotrophs without the support of paraffin or other additives. Thus, in some embodiments, oxygen and methane may be delivered to the organism to support acceptable growth rates and cell accumulation levels without using paraffin.

The cell-free biotransformation processes provided herein may be used to produce biofuel or other chemical compounds at a production rate of at least 1 g/L-h, at least 5 g/L-h, at least 10 g/L-h, at least 15 g/L-h, or at least 25 g/L-h. For example, the biofuel or other chemical compound may be produced at a rate of 0.5 g/L-h, 1 g/L-h, 2 g/L-h, 3 g/L-h, 4 g/L-h, 5 g/L-h, 6 g/L-h, 7 g/L-h, 8 g/L-h, 9 g/L-h, 10 g/L-h, 11 g/L-h, 12 g/L-h, 13 g/L-h, 14 g/L-h, 15 g/L-h, 16 g/L-h, 17 g/L-h, 18 g/L-h, 19 g/L-h, 20 g/L-h, 21 g/L-h, 22 g/L-h, 23 g/L-h, 24 g/L-h, 25 g/L-h, or more. In some embodiments, the biofuel or other chemical compound may be produced at a rate of 1 to 5 g/L-h, 1 to 10 g/L-h, 1 to 25 g/L-h, 5 to 10 g/L-h, 5 to 25 g/L-h, or 10 to 25 g/L-h.

Large-Scale Production

Some aspects of the invention relate to large-scale (e.g., using reaction volumes of greater than 10 L) production of biofuels (e.g., isobutanol) or other chemical compounds. Prior to the invention, several factors prevented the application of cell-free biotransformation to, for example, industrial and/or commercial processes. Such factors included the inability to control the redox balance in cell-free systems and the lack of molecular biology tools that would enable the rapid and efficient control of carbon flux. The present disclosure enables the use of enzymes from various microorganisms in a fully controlled and tailored environment capable of processing natural gas, in particular methane, into high-value chemicals, such as, for example, isobutanol.

In some embodiments, cell-free biotransformation reactions are conducted using reaction volumes (e.g., in a bioreactor) of 10 L to 1,000 L. For example, reaction volumes may be 10 L to 100 L, 10 L to 500 L, 100 L to 500 L, 100 L to 1000 L, or 500 L to 1000 L.

In some embodiments, cell-free biotransformation processes provided herein are used to produce at least 1 L of isobutanol per week. In some embodiments, cell-free biotransformation processes provided herein are used to produce 1 to 100 metric tons of isobutanol per week. For example, a cell-free system may be used to produce 10, 20, 30, 40, 50, 60, 70, 80, 90, or 100 metric tons of isobutanol per week.

Flexible Feedstock in Cell Free Systems

Cell-free systems enable complete decoupling of cell growth from target production. Typical challenges encountered when using mixed carbon sources (e.g., glucose and xylose as mixed C6 and C5 sugars from lignocellulosic biomass) in bioproduction include catabolite repression, membrane transport, and cytotoxicity. Cell-free systems avoid these issues, enabling more efficient use of these inexpensive sugar sources. Use of other technologies such as protease targeting enables efficient simultaneous utilization of C5 and C6 sugars for target molecule carbon skeletons as well as for sources of energy and reducing equivalents.

The following examples of isoprene production are included: (i) mixed C6 (glucose) and C1 (methane) feedstocks, and (ii) C1 (methane) feedstock.

What is claimed is:

1. A cell-free method for large-scale conversion of methane to pyruvate, comprising:
combining, in a bioreactor, methane, oxygen, and a cell lysate mixture of at least two cell lysates, at least one of which is obtained from recombinant cells, wherein the cell lysate mixture contains the following enzymes: a methane monooxygenase, a methanol dehydrogenase, a hexulose-6-phosphate synthase, a 6-phospho-3-hexuloisomerase, a 6-phosphofructokinase, a fructose bisphosphate aldolase, a triose phosphate isomerase, a transketolase, a ribose-5-phosphate isomerase or a ribulose-5-phosphate 3-epimerase, a glyceraldehyde 3-phosphate dehydrogenase, a phosphoglycerate kinase, a phosphoglycerate mutase, an enolase, and a pyruvate kinase, wherein the recombinant cells overexpress at least one of the foregoing enzymes, to form a cell-free reaction mixture; and
incubating under suitable conditions the cell-free reaction mixture to convert methane to pyruvate, thereby producing pyruvate at a production rate of at least 1 g/L-h.

2. The cell-free method of claim 1, wherein the cell lysate mixture further contains an acetolactate synthase, an acetohydroxy acid isomeroreductase, a dihydroxy acid dehydratase, an alpha-ketoisovalerate decarboxylase, and an isobutanol dehydrogenase, and wherein the method results in the conversion of pyruvate to isobutanol.

3. The cell-free method of claim 2, wherein
(i) the methane monooxygenase has EC number 1.14.13.25 or 1.14.18.3,
(ii) the methanol dehydrogenase has EC number 1.1.1.244, 1.1.2.7, or 1.1.99.37,
(iii) the hexulose-6-phosphate synthase has EC number 4.1.2.43,
(iv) the 6-phospho-3-hexuloisomerase has EC number 5.3.1.27,
(v) the 6-phosphofructokinase has EC number 2.7.1.11,
(vi) the fructose bisphosphate aldolase has EC number 4.1.2.13,
(vii) the triose phosphate isomerase has EC number 5.3.1.1,
(viii) the transketolase has EC number 2.2.1.1,
(xi) the ribose-5-phosphate isomerase has EC number 5.3.1.6, or the ribulose-5-phosphate 3-epimerase has EC number 5.1.3.1,
(xii) the glyceraldehyde 3-phosphate dehydrogenase has EC number 1.2.1.12,
(xiii) the phosphoglycerate kinase has EC number 2.7.2.3,
(xiv) the phosphoglycerate mutase has EC number 5.4.2.11 or 5.4.2.12,
(xv) the enolase has EC number 4.2.1.11,
(xvi) the pyruvate kinase has EC number 2.7.1.40,
(xvii) the acetolactate synthase has EC number 2.2.1.6,
(xviii) the acetohydroxy acid isomeroreductase has EC number 1.1.1.86,
(xix) the dihydroxy acid dehydratase has EC number 4.2.1.9,
(xx) the alpha-ketoisovalerate decarboxylase has EC number 4.1.1.72, and
(xxi) the isobutanol dehydrogenase has EC number 1.1.1.1.

4. The cell-free method of claim 2, wherein the pressure in the bioreactor is at least 1 bar.

5. The cell-free method of claim 4, wherein the pressure in the bioreactor is at least 2 bar.

6. The cell-free method of claim 2, wherein the isobutanol is produced at a production rate of at least 1 g/L-h.

7. The cell-free method of claim 6, wherein the isobutanol is produced at a production rate of at least 10 g/L-h.

8. The cell-free method of claim 2, wherein the bioreactor comprises a gas phase and an aqueous phase.

9. The cell-free method of claim 8, wherein the bioreactor further comprises an organic solvent.

10. The cell-free method of claim 9, wherein the organic solvent is selected from the group consisting of pentane, hexane, heptane, octane, nonane, and decane.

11. The cell-free method of claim 2, wherein the methane monooxygenase is obtained from a methanotroph.

12. The cell-free method of claim 11, wherein the methanotroph is a *Methylococcus capsulatus* Bath methanotroph.

13. The method of claim 2, wherein the methanol dehydrogenase is a heterologous NAD-linked methanol dehydrogenase.

14. The method of claim 13, wherein the heterologous NAD-linked methanol dehydrogenase is a heterologous *Bacillus methanolicus* NAD-linked methanol dehydrogenase.

15. The cell-free method of claim 2, wherein the recombinant cells are derived from recombinant bacteria.

16. The cell-free method of claim 15, wherein the recombinant bacteria are recombinant *Escherichia coli*.

17. The cell-free method of claim 1, wherein
(i) the methane monooxygenase has EC number 1.14.13.25 or 1.14.18.3,
(ii) the methanol dehydrogenase has EC number 1.1.1.244, 1.1.2.7, or 1.1.99.37,
(iii) the hexulose-6-phosphate synthase has EC number 4.1.2.43,
(iv) the 6-phospho-3-hexuloisomerase has EC number 5.3.1.27,
(v) the 6-phosphofructokinase has EC number 2.7.1.11,
(vi) the fructose bisphosphate aldolase has EC number 4.1.2.13,
(vii) the triose phosphate isomerase has EC number 5.3.1.1,
(viii) the transketolase has EC number 2.2.1.1,
(xi) the ribulose-5-phosphate 3-isomerase has EC number 5.3.1.6, or the ribulose-5-phosphate 3-epimerase has EC number 5.1.3.1,
(xii) the glyceraldehyde 3-phosphate dehydrogenase has EC number 1.2.1.12,
(xiii) the phosphoglycerate kinase has EC number 2.7.2.3,
(xiv) the phosphoglycerate mutase has EC number 5.4.2.11 or 5.4.2.12,
(xv) the enolase has EC number 4.2.1.11, and
(xvi) the pyruvate kinase has EC number 2.7.1.40.

18. The cell-free method of claim 1, wherein the pressure in the bioreactor is at least 1 bar.

19. The cell-free method of claim 18, wherein the pressure in the bioreactor is at least 2 bar.

20. The cell-free method of claim 1, wherein the pyruvate is produced at a production rate of at least 10 g/L-h.

21. The cell-free method of claim 1, wherein the bioreactor comprises a gas phase and an aqueous phase.

22. The cell-free method of claim 21, wherein the bioreactor further comprises an organic solvent.

23. The cell-free method of claim 22, wherein the organic solvent is selected from the group consisting of pentane, hexane, heptane, octane, nonane, and decane.

24. The cell-free method of claim 1, wherein the methane monooxygenase is obtained from a methanotroph.

25. The cell-free method of claim 24, wherein the methanotroph is a *Methylococcus capsulatus* Bath methanotroph.

26. The method of claim 1, wherein the methanol dehydrogenase is a heterologous NAD-linked methanol dehydrogenase.

27. The method of claim 26, wherein the heterologous NAD-linked methanol dehydrogenase is a heterologous *Bacillus methanolicus* NAD-linked methanol dehydrogenase.

28. The cell-free method of claim 1, wherein the recombinant cells are recombinant bacteria.

29. The cell-free method of claim 28, wherein the recombinant bacteria are recombinant *Escherichia coli*.

* * * * *